US011331373B2

(12) United States Patent
Zuo et al.

(10) Patent No.: US 11,331,373 B2
(45) Date of Patent: May 17, 2022

(54) COMBINATION THERAPY FOR TREATING DISORDERS OF THE EAR

(71) Applicant: ST. JUDE CHILDREN'S RESEARCH HOSPITAL, Memphis, TN (US)

(72) Inventors: Jian Zuo, Memphis, TN (US); Fei Zheng, Memphis, TN (US); Tetsuji Yamashita, Memphis, TN (US); Wanda Layman, Germantown, TN (US)

(73) Assignee: St. Jude Children's Research Hospital, Memphis, TN (US)

( * ) Notice: Subject to any disclaimer, the term of this patent is extended or adjusted under 35 U.S.C. 154(b) by 319 days.

(21) Appl. No.: 16/483,654

(22) PCT Filed: Jan. 31, 2018

(86) PCT No.: PCT/US2018/016085
§ 371 (c)(1),
(2) Date: Aug. 5, 2019

(87) PCT Pub. No.: WO2018/148071
PCT Pub. Date: Aug. 16, 2018

(65) Prior Publication Data
US 2019/0358293 A1 Nov. 28, 2019

Related U.S. Application Data

(60) Provisional application No. 62/504,783, filed on May 11, 2017, provisional application No. 62/457,487, filed on Feb. 10, 2017.

(51) Int. Cl.
| | | |
|---|---|---|
| *C12N 15/11* | (2006.01) | |
| *A61K 38/17* | (2006.01) | |
| *A01K 67/027* | (2006.01) | |
| *A61K 9/00* | (2006.01) | |
| *A61K 31/7105* | (2006.01) | |
| *A61K 45/06* | (2006.01) | |

(52) U.S. Cl.
CPC ...... *A61K 38/1709* (2013.01); *A01K 67/0275* (2013.01); *A61K 9/0046* (2013.01); *A61K 31/7105* (2013.01); *A61K 45/06* (2013.01); *A01K 2217/052* (2013.01); *A01K 2217/206* (2013.01); *A01K 2227/105* (2013.01)

(58) Field of Classification Search
CPC .. A61K 9/0046; A61K 48/00; C12N 2501/60; C12N 5/062; C12N 5/0627
See application file for complete search history.

(56) References Cited

U.S. PATENT DOCUMENTS

| | | |
|---|---|---|
| 7,825,099 B2 | 11/2010 | Feinstein |
| 9,149,024 B2 | 10/2015 | Huang |
| 9,434,946 B2 | 9/2016 | Adamsky |
| 2004/0166091 A1* | 8/2004 | Brough ............... A61K 48/005 424/93.2 |
| 2005/0287127 A1 | 12/2005 | Li |
| 2012/0020774 A1 | 1/2012 | Bart |
| 2012/0222141 A1* | 8/2012 | Huang ................. A61K 9/0046 800/9 |
| 2015/0050354 A1 | 2/2015 | Bouchon |
| 2015/0306178 A1 | 10/2015 | Meyer |

FOREIGN PATENT DOCUMENTS

| | | |
|---|---|---|
| WO | 2000073764 A2 | 12/2000 |
| WO | 2004076626 A2 | 9/2004 |
| WO | 2011005496 A2 | 1/2011 |
| WO | 2011153348 A2 | 12/2011 |
| WO | 2013020097 A1 | 2/2013 |
| WO | 2013134022 A1 | 9/2013 |
| WO | 2014145205 A2 | 9/2014 |
| WO | 2014197421 A1 | 12/2014 |
| WO | 2015048577 A2 | 4/2015 |

OTHER PUBLICATIONS

Chellappa, R., S. Li, S. Pauley, I. Jahan, K. Jin, and M. Xiang (2008) Mol. Cell Biol. "Barhl1 regulatory sequences required for cell-specific gene expression and autoregulation in the inner ear and central nervous system," 28 (6):1905-1914.
Chonko, K.T, I. Jahan, J. Stone, M.C. Wright, T. Fujiyama, M. Hoshino, B. Fritzsch and S.M. Maricich (2013) "Atoh1 directs hair cell differentiation and survival in the late embryonic mouse inner ear," Dev. Biol. 381(2):401-410.
Costa, A., L. Sanches-Guardado, S. Juniat, J.E. Gale, N. Daudet and D. Henrique (2015) "Generation of sensory hair cells by genetic programming with a combination of transcription factors," Development 142(11):1948-1959.
Golden, E.J., A. Benito-Gonzalez and A. Doetzlhofer (2015) "The RNA-binding protein LIN28B regulates developmental timing in the mammalian cochlea," Proc. Natl. Acad. Sci. USA 112:E3864-73.
Gubbels, S.P., D.W. Woessner, J.C. Mitchell, A.J. Ricci and J.V. Brigande (2008) "Functional auditory hair cells produced in the mammalian cochlea by in utero gene transfer," Nature 455(7212):537-41.
Ikeda, R., K. Pak, E. Chavez, and A.F. Ryan (2015) "Transcription factors with conserved binding sites near ATOH1 on the POU4F3 gene enhance the induction of cochlear hair cells," Mol. Neurobiol. 51(2):672-684.
International Preliminary Report on Patentability in PCT/US2018/16085 dated Aug. 22, 2019.
International Search Report and Written Opinion in PCT/US2018/16085 dated May 24, 2018.

(Continued)

*Primary Examiner* — Dana H Shin
(74) *Attorney, Agent, or Firm* — Veritay Group IP, PLLC; Susan Fentress; Liam O'Donnell

(57) ABSTRACT

Methods and compositions using a nucleic acid molecule encoding an atonal-associated factor in combination with a co-transcription factor and/or inhibitor of a gene silencing complex to change the sensory perception of an animal are described.

1 Claim, No Drawings

Specification includes a Sequence Listing.

(56) References Cited

OTHER PUBLICATIONS

Jahan, I., N. Pan, J. Kersigo, L.E. Calisto, K.A. Morris, B. Kopecky, J.S. Duncan, K.W. Beisel, and B. Fritzsch (2012) "Expression of neurog1 instead of atoh1 can partially rescue organ of corti cell survival," PLoS ONE 7(1):e30853.

Kelly, M.C., Q. Chang, A. Pan, X. Lin, and P. Chen (2012) "Atoh1 directs the formation of sensory mosaics and induces cell proliferation in the postnatal mammalian cochlea in vivo," J. Neurosci. 32(19):6699-6710.

Liang, J., D. Wang, G. Renaud, T.G. Wolfsberg, A.F. Wilson, and S.M. Burgess (2012) "The stat3/socs3a pathway is a key regulator of hair cell regeneration in zebrafish," J. Neurosci. 32(31):10662-10673.

Liu, Z., J.A. Dearman, B.C. Cox, B.J. Walters, L. Zhang, O. Ayrault, F. Zindy, L. Gan, M.F. Roussel, J. Zuo (2012) "Age-dependent in vivo conversion of mouse cochlear pillar and Deiters' cells to immature hair cells by Atoh1 ectopic expression," J. Neurosci. 32(19):6600-6610.

Liu, Z., J. Fang, J. Dearman, L. Zhang, and J. Zuo (2014) "In vivo generation of immature inner hair cells in neonatal mouse cochleae by ectopic Atoh1 expression," PLoS One 9(2):e89377.

Walters, B.J., E. Coak, J. Dearman, G. Bailey, T. Yamashita, B. Kuo and J. Zuo (2017) "In Vivo Interplay between p27Kip1, GATA3, ATOH1, and POU4F3 Converts Non-sensory Cells to Hair Cells in Adult Mice," Cell Reports 19:307-320.

Wilson, T., I. Omelchenko, S. Foster, Y. Zhang, X. Shi and A.L. Nuttall (2014) "JAK2/STAT3 Inhibition Attenuates Noise-Induced Hearing Loss," PLoS ONE 9(10):e108276.

\* cited by examiner

COMBINATION THERAPY FOR TREATING DISORDERS OF THE EAR

INTRODUCTION

This application is a U.S. National Stage Application of PCT/US2018/016085 filed Jan. 31, 2018 and claims the benefit of priority from U.S. Patent Application Ser. Nos. 62/504,783, filed May 11, 2017 and 62/457,487, filed Feb. 10, 2017, the contents of each of which are incorporated herein by reference in their entireties.

This invention was made with government support under Grant Numbers DC006471 DC015010, DC015444, DC013879, DC013232, and CA021765 awarded by the National Institutes of Health and Grant Numbers N00014-09-V-1014, N00014-12-V-0191, N00014-12-V-0775, and N00014-16-V-2315 awarded by the Office of Naval Research. The government has certain rights in the invention.

BACKGROUND

The ear is a complex organ composed of a labyrinth of structures responsible for hearing and balance. Perception of both hearing and balance lies in the ability of inner ear structures to transform mechanical stimuli to impulses recognized by the brain. The sensory receptors responsible for hearing are located in the cochlea, a spiral-shaped canal filled with fluid. Within the cochlea is the organ of Corti, which is lined with columnar sensory hair cells bridging the basilar membrane and the tectorial membrane. As sound waves pass through the organ of Corti, the basilar membrane vibrates causing the hair cells to bend back and forth. The movement depolarizes the hair cell, leading to release of neurotransmitters to the auditory nerve, which carries the impulse to the brain.

The inner-ear cochlear sensory epithelium is post-mitotic after birth and, in mice, exhibits only limited spontaneous regeneration during the first week after birth. Atonal BHLH Transcription Factor 1 (Atoh1), a lineage-specific transcription factor for sensory hair cells, directly converts non-sensory supporting cells to sensory hair cells in cochlear explant culture and in vivo (Gubbels, et al. (2008) *Nature* 455(7212):537-41; Kelly, et al. (2012) *J. Neurosci.* 32(19): 6699-710; Liu, et al. (2012) *J. Neurosci.* 32(19):6600-10; Liu, et al. (2014) *PLoS One* 9(2):e89377; Zheng & Gao (2000) *Nature Neurosci.* (6):580-6). Further, the FDA has approved a clinical trial (NCT02132130) for assessing safety, tolerability and efficacy of CGF166, a recombinant adenovirus 5 (Ad5) vector containing a cDNA encoding the human Atoh1. However, it is not clear whether Atoh1-mediated non-sensory supporting cell-to-sensory hair cell conversion in vivo is efficient and complete and whether such conversion bypasses the progenitor-cell state or follows normal developmental lineage paths precisely. In several mouse models, Atoh1-converted sensory hair cells exhibited immature hair cell morphology and did not express several terminal differentiation markers (e.g., Slc26a5 encoding prestin and Ocm encoding oncomodulin), and the conversion rate was low (6%-20%) (Kelly, et al. (2012) *J. Neurosci.* 32(19):6699-710; Liu, et al. (2012) *J. Neurosci.* 32(19): 6600-10; Liu, et al. (2014) *PLoS One* 9(2):e89377). Therefore, the identity of additional factors to improve efficiency and completion are needed.

SUMMARY OF THE INVENTION

The invention provides a method of improving the sensory perception of an animal by administering to the inner ear of an animal in need thereof an expression vector harboring a nucleic acid molecule encoding an atonal-associated factor in combination with at least one co-transcription factor and/or inhibitor of a gene silencing complex. In some embodiments, the at least one co-transcription factor is Sox9, Sall2, Camta1, Hey2, Gata2, Hey1, Lass2, Sox10, Gata3, Cux1, Nr2f1, Hes1, Rorb or Jun; Zfp667, Lhx3, Nhlh1, Mdx4, Zmiz1, Myt1, Stat3, Barh11, Tox, Prox1, Nfia, Thrb, Mycl1, Kdm5a, Creb314, Etv1, Peg3 or Bach2; Isl1, Zbtb38, Lbh, Tub, Hmg20, Rest, Zfp827, Aff3, Pknox2, Arid3b, Mlxip, Zfp532, Ikzf2, Sall1, Six2 or Sall3; Lin28b, Pou4f3 or Rfx7; or a combination thereof. In other embodiments, the inhibitor of the gene silencing complex inhibits the activity of a subunit of a Nucleosome Remodeling and Deacetylation complex, e.g., Lsd1, or Polycomb Repressive Complex 2, e.g., Eed. In certain embodiments, the inhibitor is an inhibitory RNA, small organic molecule, antibody or gene editing. A pharmaceutical composition and kit are also provided.

DETAILED DESCRIPTION OF THE INVENTION

Atonal-associated factors promote the differentiation of non-sensory cells of the sensory epithelium, i.e., supporting cells, into sensory hair cells. It has now been found that Atonal-associated factor gene therapy in combination with overexpression of Isl1 (ISL LIM Homeobox 1) and/or loss in Eed (Embryonic Ectoderm Development) or loss in Lsd1 (Lysine-Specific Demethylase 1A, also known as KMD1) expression can facilitate regeneration of functional hair cells and hearing restoration. Accordingly, this inventive is a method for generating a hair cell from a differentiated progenitor cell using Atonal-associated factor gene therapy in combination with a co-transcription factor and/or inhibitor of a gene silencing complex. The generation of sensory hair cells in the inner ear is exploited to modulate the sensory perception of an animal. Ideally, the inventive method prophylactically or therapeutically treats an animal, preferably a mammal (e.g., a human), for at least one disorder associated with loss or damage of sensory hair cells, e.g., disorders of the ear associated with damage of sensory hair cells (such as hearing loss or balance disorders). The inventive method also is useful in maintaining a level of sensory perception, i.e., controlling the loss of perception of environmental stimuli caused by, for instance, the aging process. The invention further provides materials for modulating or improving the sensory perception of an animal.

Atonal-Associated Factor.

Atonal-associated factors are a family of transcription factors that transdifferentiate supporting cells into sensory hair cells in the ear. Atonal-associated factors are transcription factors of the basic helix-loop-helix (bHLH) family of proteins. The basic domain of the protein is responsible for DNA binding and function of the protein. The *Drosophila* bHLH protein (ato) activates genes associated with the development of sensory organs of the insect, specifically chordotonal organs. Atonal-associated factors also referred to as Atonal Homolog 1 (Atoh1) proteins are found in a variety of animals and insects, including mice (mouse atonal homolog 1 (Math1)), chickens (chicken atonal homolog 1 (Cath1)), *Xenopus* (*Xenopus* atonal homolog 1 (Xath1)), and humans (human atonal homolog 1 (Hath1)). Math1 is highly homologous to ato in the bHLH domain (82% amino acid similarity) with 100% conservation of the basic domain, and functions in determining cell fate in mice. Math1 has been shown to be essential for hair cell development and can stimulate hair cell regeneration in the ear. Math1 is further characterized in, for example, Ben-Arie, et al. (1996) *Human Mol. Genet.* 5:1207-1216; Bermingham, et al. (1999) *Science* 284:1837-1841; Zheng & Gao (2000) *Nature Neurosci.* 3(2):580-586; and Chen, et al. (2002) *Development* 129:2495-2505. Hath1 is the human counterpart of Math1. In certain embodiments, the atonal-associated factor is Math1 or Hath1 or a protein sharing significant amino acid sequence similarity with that of Math1 and Hath1. Atonal-associated factors are further described in WO 2000/73764.

The amino acid sequence of Hath1 and Math1 are known in the art and available under GENBANK Accession Nos. NP_005163 (Gene ID:474) and NP_031526 (Gene ID: 11921), respectively. A protein having significant amino acid sequence similarity with that of Math1 and Hath1 desirably has an amino acid sequence that is at least about 50% identical to the amino acid sequence of Hath1 (NP_005163) or Math1 (NP_031526), and has the ability to transdifferentiate supporting cells into sensory hair cells. Ideally, the Atonal-associated factor has at least about 60% amino acid sequence identity (e.g., at least about 65%, or at least about 70%, sequence identity), preferably at least about 75% amino acid sequence identity (e.g., at least about 80%, or at least about 85%, sequence identity), and most preferably at least about 90% amino acid sequence identity (e.g., at least about 95% sequence identity) with the Hath1 (NP_005163) or Math1 (NP_031526) amino acid sequence. Looking to the nucleic acid sequence encoding the Atonal-associated factor, preferably the nucleic acid sequence encodes the Hath1 (NP_005163) or Math1 (NP_031526) amino acid sequence (i.e., the portion of the Hath1 or Math1 genes that encode the Hath1 and Math1 proteins absent the regulatory sequences associated with the gene) or cDNA encoding the Hath1 or Math1 protein. Nucleic acid sequences encoding Hath1 and Math1 are publicly available under GENBANK Accession Nos. NM_005172 and NM_031526, respectively.

While wild-type Hath1 or Math1 proteins and nucleic acids are particularly useful, many modifications and variations (e.g., mutation) of the Hath1 or Math1 sequences are possible and appropriate in the context of the invention. For example, the degeneracy of the genetic code allows for the substitution of nucleotides throughout the coding sequence, as well as in the translational stop signal, without alteration of the encoded polypeptide. Such substitutable sequences can be deduced from the known amino acid sequence of an atonal-associated factor or nucleic acid sequence encoding an atonal-associated factor and can be constructed by conventional synthetic or site-specific mutagenesis procedures. Synthetic DNA methods can be carried out in substantial accordance with the procedures of Itakura, et al. (1977) *Science* 198:1056-1063 or Crea, et al. (1978) *Proc. Natl. Acad. Sci. USA* 75:5765-5769. Site-specific mutagenesis procedures are described in Maniatis, et al. (1989) *Molecular Cloning: A Laboratory Manual*, 2$^{nd}$ Ed., Cold Spring Harbor, N.Y. Alternatively, the nucleic acid sequence can encode an atonal-associated peptide with extensions on either the N- or C-terminus of the protein, so long as the resulting atonal-associated factor retains activity (i.e., the ability to transdifferentiate supporting cells into sensory hair cells).

The function of atonal-associated factors is dependent on the helix-loop-helix (HLH) portion of the protein, particularly the basic region of the HLH domain (Chien, et al. (1996) *Proc. Natl. Acad. Sci.* 93:13239-13244), which includes the amino acid sequence AANARERRRMHGLN-HAFDQLR (SEQ ID NO:1). Accordingly, any modification of the atonal-associated factor amino acid sequence desirably is located outside of the basic domain of the protein. Exemplary constructs and expression vectors harboring nucleic acids encoding atonal-associated factor are provided WO 2004/076626.

Co-Transcription Factors.

Early in the conversion process, the upregulation or ectopic expression of HC lineage-specific transcription factors, such as Atoh1, in SCs triggers the initial loss of SC identity, concomitant with an increase in HC identity, by inducing genes involved in defining HC morphology and function (such as Pou4f3 and other HC early markers). This initial process is Atoh1-dose dependent and is quite uniform across most SCs, but subsequent epigenetic or other cofactors silence the initiation in more than 80% of SCs, thereby reducing the conversion efficiency to between 6% and 20%, despite the persistent expression of Atoh1 (Stajanova, et al. (2016) *Development* 143(9):1632). With Atoh1 alone, the initial conversion drives a gradual continuum of conversion towards HC identity until it is stalled in most converted cells at intermediate states between donor SCs and target HCs that resemble P0-7 differentiating HCs, thereby bypassing the otic progenitor state. To counter the silencing in many SCs and to push cHCs forward from these intermediate states to avoid their either diverging into another target-cell state or reverting to SC states, additional factors are required, such as co-transcription factors identified herein. Synergistically, Atoh1 and these other transcription factors can enhance the conversion efficiency and eventually promote prestin, oncomodulin and/or vGlut3 expression to enable the complete maturation of converted HCs.

Accordingly, the term "co-transcription factor" is used herein to refer to a transcription factor that synergistically enhances Atoh1-mediated SC-to-HC conversion, e.g., by increasing the conversion rate. For the purposes of this invention, approximately 50 other transcription factors have been identified as being differentially expressed in cHCs, SCs, and mature HC and serve as co-transcription factors of Atoh1. A list of co-transcription factors of use in this invention are provided in Table 1.

TABLE 1

| Group | Co-transcription Factor | GENBANK Accession No. Nucleotide Sequence | Protein Sequence |
|---|---|---|---|
| 1 | Sox9, SRY (Sex-Determining Region Y)-Box 9 | NM_000346 | NP_000337 |
| 1 | Sall2, Spalt Like Transcription Factor 2 | NM_001291446 NM_001291447 NM_005407 | NP_001278375 NP_001278376 NP_005398 |
| 1 | Camta1, Calmodulin Binding Transcription Activator 1 | NM_001195563 NM_001242701 NM_001349608 NM_015215 | NP_001182492 NP_001229630 NP_001336537 NP_056030 |

TABLE 1-continued

| Group | Co-transcription Factor | GENBANK Accession No. Nucleotide Sequence | GENBANK Accession No. Protein Sequence |
|---|---|---|---|
| 1 | Hey2, Hes (Hairy/Enhancer-of-Split) Related Family BHLH Transcription Factor With YRPW Motif 2 | NM_012259 | NP_036391 |
| 1 | Gata2, GATA Binding Protein 2 | NM_001145661 NM_001145662 NM_032638 | NM_001145661 NP_001139134 NP_116027 |
| 1 | Hey1, Hes Related Family BHLH Transcription Factor With YRPW Motif 1 | NM_001040708 NM_001282851 NM_012258 | NP_001035798 NP_001269780 NP_036390 |
| 1 | Lass2, longevity assurance homolog 2, (aka, CERS2, ceramide synthase 2) | NM_022075 NM_181746 | NP_071358 NP_859530 |
| 1 | Sox10, SRY-Box 10 | NM_006941 | NP_008872 |
| 1 | Gata3, GATA Binding Protein 3 | NM_001002295 NM_002051 | NP_001002295 NP_002042 |
| 1 | Cux1, Cut Like Homeobox 1 | NM_181552 NM_001913 NM_181500 NM_001202543 | NP_853530 NP_001904 NP_852477 NP_001189472 |
| 1 | Nr2f1, Nuclear Receptor Subfamily 2 Group F Member 1 | NM_005654 | NP_005645 |
| 1 | Hes1, Hes Family BHLH Transcription Factor 1 | NM_005524 | NP_005515 |
| 1 | Jun, Jun Proto-Oncogene, AP-1 Transcription Factor Subunit | NM_002228 | NP_002219 |
| 1 | Rorb, RAR Related Orphan Receptor | NM_006914 | NP_008845 |
| 2 | Zfp667, Zinc Finger Protein 667 | NM_001321355 NM_001321356 NM_022103 | NP_001308284 NP_001308285 NP_071386 |
| 2 | Lhx3, LIM Homeobox 3 | NM_014564 NM_178138 | NP_055379 NP_835258 |
| 2 | Nhlh1, Nescient Helix-Loop-Helix 1 | NM_005598 | NP_005589 |
| 2 | Mxd4, MAX Dimerization Protein 4 | NM_006454 | NP_006445 |
| 2 | Zmiz1, Zinc Finger MIZ-Type Containing 1 | NM_020338 | NP_065071 |
| 2 | Myt1, Myelin Transcription Factor 1 | NM_004535 | NP_004526 |
| 2 | Stat3, Signal Transducer And Activator Of Transcription 3 | NM_003150 NM_139276 NM_213662 | NP_003141 NP_644805 NP_998827 |
| 2 | Barhl1, BarH Like Homeobox 1 | NM_020064 | NM_020064 |
| 2 | Tox, Thymocyte Selection Associated High Mobility Group Box | NM_014729 | NP_055544 |
| 2 | Prox1, Prospero Homeobox 1 | NM_001270616 NM_002763 | NP_001257545 NP_002754 |
| 2 | Nfia, Nuclear Factor I A | NM_001134673 NM_001145511 NM_001145512 NM_005595 | NP_001128145 NP_001138984 NP_001138983 NP_005586 |
| 2 | Thrb, Thyroid Hormone Receptor Beta | NM_000461 NM_001128176 NM_001128177 NM_001252634 | NP_000452 NP_001121648 NP_001121649 NP_001239563 |
| 2 | Mycl1, V-Myc Avian Myelocytomatosis Viral Oncogene Lung Carcinoma Derived Homolog | NM_001033081 NM_001033082 NM_005376 | NP_001028253 NP_001028254 NP_005367 |
| 2 | Kdm5a, Lysine Demethylase 5A | NM_001042603 | NP_001036068 |

TABLE 1-continued

| Group | Co-transcription Factor | GENBANK Accession No. Nucleotide Sequence | GENBANK Accession No. Protein Sequence |
|---|---|---|---|
| 2 | Bach2, BTB Domain And CNC Homolog 2 | NM_001170794 NM_021813 | NP_001164265 NP_068585 |
| 2 | Creb3l4, CAMP Responsive Element Binding Protein 3 Like 4 | NM_001255978 NM_001255979 NM_001255980 NM_001255981 NM_130898 | NP_001242907 NP_001242908 NP_001242909 NP_001242910 NP_570968 |
| 2 | Etv1, ETS Variant 1 | NM_001163147 NM_001163148 NM_001163149 NM_004956 | NP_001156619 NP_001156620 NP_001156621 NP_004947 |
| 2 | Peg3, Paternally Expressed 3 | NM_001146184 NM_001146185 NM_001146186 NM_001146187 NM_006210 | NP_001139656 NP_001139657 NP_001139658 NP_001139659 NP_006201 |
| 3 | Isl1, ISL LIM Homeobox 1 | NM_002202 | NP_002193 |
| 3 | Zbtb38, Zinc Finger And BTB Domain Containing 38 | NM_001080412 NM_001350099 NM_001350100 | NP_001073881 NP_001337028 NP_001337029 |
| 3 | Lbh, Limb Bud And Heart Development | NM_030915 | NP_112177 |
| 3 | Tub, Tubby Bipartite Transcription Factor | NM_003320 NM_177972 | NP_003311 NP_813977 |
| 3 | Hmg20a, High Mobility Group 20A | NM_001304504 NM_001304505 NM_018200 | NP_001291433 NP_001291434 NP_060670 |
| 3 | Rest, RE1 Silencing Transcription Factor | NM_001193508 NM_005612 | NP_001180437 NP_005603 |
| 3 | Zfp827, Zinc Finger Protein 827 | NM_001306215 NM_178835 | NP_001293144 NP_849157 |
| 3 | Aff3, AF4/FMR2 Family Member 3 | NM_001025108 NM_002285 | NP_001020279 NP_002276 |
| 3 | Pknox2, PBX/Knotted 1 Homeobox 2 | NM_022062 | NP_071345 |
| 3 | Arid3b, AT-Rich Interaction Domain 3 | NM_001307939 NM_006465 | NP_001294868 NP_006456 |
| 3 | Mlxip, MLX Interacting Protein | NM_014938 | NP_055753 |
| 3 | Zfp532, Zinc Finger Protein 532 | NM_001318726 NM_001318727 NM_001318728 NM_018181 | NP_001305655 NP_001305656 NP_001305657 NP_060651 |
| 3 | Ikzf2, IKAROS Family Zinc Finger 2 | NM_001079526 NM_016260 | NP_001072994 NP_057344 |
| 3 | Sall1, Spalt Like Transcription Factor 1 | NM_001127892 NM_002968 | NP_001121364 NP_002959 |
| 3 | Six2, SIX Homeobox 2 | NM_016932 | NP_058628 |
| 3 | Sall3, Spalt Like Transcription Factor 3 | NM_171999 | NP_741996 |
| 4 | Lin28b, Lin-28 Homolog B | NM_001004317 | NP_001004317 |
| 4 | Pou4f3, POU Class 4 Homeobox 3 | NM_002700 | NP_002691 |
| 4 | Rfx7, Regulatory Factor X7 | NM_022841 | NP_073752 |

Ideally, one or more of the co-transcription factors of Table 1 (e.g., 1, 2, 3, 4, 5, 6, 7, 8, 9, 10 or more) can be provided in combination with Atoh1 in the form of nucleic acid molecules that are co-expressed with Atoh1, either by the same or different expression construct or expression vector. Moreover, expression of the co-transcription factor(s) can be achieved using the same or different promoter as that used in the expression of Atoh1.

Sox9 is widely expressed in the otic epithelium, periotic mesenchyme and cartilaginous otic capsule (Mak, et al. (2009) *Gene Expr. Patterns* 9(6):444-453). During differentiation of Corti, Sox9 is progressively restricted to supporting cells and its expression is absent in hair cells. When overexpressed in P12 utricles in vitro, it has been shown that Sox9 has no effect on supporting cell proliferation (Gnedeva & Hudspeth (2015) *Proc. Natl. Acad. Sci. USA* 112(45): 14066-14071). Further, it has been demonstrated by ex vivo electroporation of mouse embryonic cochlea, that Sox9 strongly inhibits hair cell fate even when it is forced by ectopic expression of Atoh1 (Huyghe, et al. (June 2013) *9th Molecular Biology of Hearing and Deafness Conference*, Palo alto, CA).

While Sall2 has been shown to have limited expression within the inner ear sensory epithelia of mice with gene expression databases (e.g., Eurexpress), its function within the inner ear of humans has not been described.

Camta1 is globally expressed in embryonic mice and becomes restricted to the cerebellum, hippocampi, and olfactory bulbs later in development. A SNP in the Camta1 gene has been identified as being associated with noise-induced hearing loss (Grondin, et al. (2015) *PLoS ONE* 10(6):e0130827). However, the function of Camta1 in the inner ear of humans has not been described.

Hey2 is expressed in the cochlear epithelium prior to terminal differentiation. Its expression is subsequently restricted to supporting cells, overlapping with the expression domains of two known Notch target genes, Hairy and enhancer of split homolog genes Hes1 and Hes5. In combination with the loss of Hes1 or Hes5, genetic inactivation of Hey2 leads to increased numbers of mis-patterned inner or outer hair cells, respectively (Li, et al. (2008) *BMC Dev. Biol.* 8:20). Inhibitory RNA targeting Hey2 have been described for use in increasing the expression of Atoh1 in human adult cochlear supporting cells (US 2012/020774; WO 2013/020097).

In hematopoietic and adipose progenitors, Gata2 is involved in maintaining the cells in an undifferentiated state, and overexpression of Gata2 promotes cell cycle progression and inhibits differentiation (Tsai, et al. (2005) *EMBO Rep.* 6:879-884; Lugus, et al. (2007) *Development* 134:393-405). Gata2 is expressed within the growing inner ear of mouse and chicken, but it has been shown to only affect vestibular morphogenesis while sensory epithelia including hair cells remain (Haugas, et al. (2010) *Dev. Dyn.* 239:2452-69; Lillevali, et al. (2004) *Dev. Dyn.* 231:775-81). When co-transfected with hATOH1, hGata2 does not alter the effects of hAtoh1 (Ikeda, et al. (2015) *Mol. Neurobiol.* 51(2):672-84).

Hey1 is highly expressed in supporting cells and HC progenitors. In addition, Hey1 and Hey2 control the spatial and temporal pattern of auditory HC differentiation downstream of Hedgehog signaling (Benito-Gonzalez Doetzlhofer (2014) *J. Neurosci.* 34(38):12865-76). Inhibitory RNA targeting Hey1 have been described for use in increasing the expression of Atoh1 in human adult cochlear supporting cells (US 2012/020774; WO 2013/020097).

Lass2 or CERS2 is involved in the synthesis of ceramides, the building blocks of all complex sphingolipids. However, the function of Lass2 in the inner ear of humans has not been described.

Sox10 is expressed in all neural crest cells and is especially crucial for specification, survival, and differentiation of Schwann cells derived from neural crest stem cells. In addition to neural crest, Sox10 is expressed early and widespread in the ear (Wakaoka, et al. (2013) *Hear. Res.* 302:17-25). Overexpression of either Sox9 or Sox10 in *Xenopus* results in ectopic otocysts (Taylor & Labonne (2005) *Dev. Cell* 9:593-603) indicating a role of Sox10 in ear development.

In inner ear development, Gata3 plays a crucial role and haploinsufficiency leads to hearing loss even in early postnatal development, which is maintained through to adulthood (van der Wees, et al. (2004) *Neurobiol. Dis.* 16(1):169-78). It has been suggested that the function of Gata3 during inner ear development may be associated with IGF signaling and AKT signaling. GATA3 deficiency leads to decreased expression of IGF1, IGF2, and several IGF-binding proteins as well as the serine-threonine kinase Akt2/PKB beta, but to increased expression of Akt1/PKB alpha protein (Milo, et al. (2009) *PLoS One* 4(9):e7144). In cochlear development, Gata3 is thought to be essential for neurosensory specification and differentiation. Gata3 deficiency leads to impaired differentiation of hair cells, with decreased hair cell differentiation in the mouse cochlea (Duncan &, Fritzsch (2013) *PLoS One* 8(4):e62046; Rivolta & Holley (1998) *J. Neurocytol.* 27(9):637-47). The expression of Gata3, either alone or in combination with Atho1, has been suggested for use in generating inner ear cells (US 2015/0050354; US 2005/0287127). Further, the when co-transfected with hATOH1 and hTCF3, hGATA3 increased the number of pou4f3/GFP+ cells (Ikeda, et al. (2015) *Mol. Neurobiol.* 51(2):672-84; Walters, et al. (2017) *Cell Reports* 19:307-320).

Mammalian cut proteins function as cell cycle-dependent transcription factors that can function as activators or repressors. The binding of Cux1 protein to the promoters of target genes appears to be limited to tissues or developmental stages in which the target genes are not expressed. Upon terminal differentiation, Cux1 is downregulated or loses the ability to bind to the promoters, permitting transcription of the target genes. Mice carrying targeted deletions of Cux1 exhibit reduced growth, retarded differentiation of lung epithelia, hair follicle defects, reduced male fertility, and deficient T and B cell function. In contrast, transgenic mice ectopically expressing Cux1 exhibit multiorgan hyperplasia including an increase in the size of the kidneys, heart, liver, and testis, apparently resulting from the repression of $p27^{kip1}$ gene expression (Ledford, et al. (2002) *Dev. Biol.* 245:157-171). When co-transfected with hATOH1, hCUX1 does not alter the effects of hAtoh1 (Ikeda, et al. (2015) *Mol. Neurobiol.* 51(2):672-84).

Nr2f1 is expressed early in the developing otic vesicle. Nr2f1 expression correlates with the differentiation of hair cells and supporting cells in the organ of Corti. Furthermore, nuclear Nr2f1 receptor protein is localized in the cytoplasm of maturing hair cells and pillar cells (Tang, et al. (2005) *Gene Expr. Patterns* 5:587-92). Further, deletion of Nr2f1 disrupts normal patterning of the sensory epithelial mosaic (Kelley (2007) *Int. J. Dev. Biol.* 51:571-583; Tang, et al. (2006) *Development* 133:3683-3693) and Nr2f1 mutants have been shown to exhibit defects in hearing (Zhou, et al. (1999) *Neuron* 24:847-59).

Mxd4 is expressed at low levels in adult mammalian HCs (Li, et al. (2016) *PLoS ONE* 11(3):e0151291). Further, Mxd4 has been identified as a direct target of Atoh1 (Klisch, et al. (2011) *Proc. Natl. Acad. Sci. USA* 208:3288-3293). However, overexpresssion of Mxd4 in the inner ear has not been described.

Hes1 has been identified as playing a role in sensory hair cell development in the cochlea and vestibular structures of the ear. Co-transfection of Kolliker's organ cells with Atoh1 and Hes1 has been shown to inhibit hair cell formation (U.S. Pat. No. 9,434,946). Further, co-transfection with hATOH1 with hHES1 has been shown to produce less pou4f3/GFP+ and myosin7A+ cells in the GER than hATOH1 alone (Ikeda, et al. (2015) *Mol. Neurobiol.* 51(2):672-84). In this respect, siRNA targeting Hes1 have been described to increase expression of Atoh1 in human adult cochlear supporting cells (US 2012/020774; WO 2013/020097; WO 2011/153348).

The JNK/c-Jun cascade has been shown to be a significant initiator of apoptosis in damaged auditory neurons (Ylikoski, et al. (2002) *Hear. Res.* 166:33-43). Neurons treated with c-jun antisense oligonucleotides were protected relative to non-treated cells (Scarpidis, et al. (2003) *Otol. Neurotol.* 24:409-17) and c-jun peptides have been suggested for use in the treatment of inner ear disorders, such as acute inner ear tinnitus (US 2015/0306178).

Zfp667 has been shown to be expressed to be expressed during enteroendocrine development. However, the function of Zfp667 in the inner ear of humans has not been described.

Lhx3 is expressed specifically in auditory and vestibular hair cells soon after terminal mitoses and persists into the adult in vestibular hair cells (Hume, et al. (2007) *Gene Expr. Patterns* 7(7):798-807). Further, Lhx3 mRNA is downregulated specifically in the cochlea hair cells in the inner ears of mice with mutation of Pou4f3, which is known to cause non-syndromic hearing loss in humans (DFNA15; MIM 602459). In this respect, mutation of Lhx3 results in sensorineural hearing loss (Rajab, et al. (2008) *Hum. Mol. Genet.* 17:2150-9). Overexpression of Lhx3 in cochlea non-sensory cells is suggested to lead to IsI1 suppression (WO 2011/005496).

Nhlh1 is expressed in hair cells and plays a role in their differentiation (Jahan, et al. (2010) *PLoS ONE* 5(7):e11661; Fritzsch, et al. (2010) *Cell Mol. Life Sci.* 67:3089-3099). Nhlh1 is downstream of Neurog1 and Atoh1 and is absent in Atoh1 conditional knockout mice but present in wild-type and heterozygous knock-in mice (Jahan, et al. (2012) *PLoS ONE* 7(1):e30853).

Zmiz1 also named ZIMP7, is a protein inhibitor of activated STAT (PIAS)-like protein and a transcriptional coactivator. Zmiz1 contains an extended SP-RING domain, in common with other PIAS proteins. In addition to this domain, Zmiz1 also contains a strong intrinsic transactivation domain through which it augments the transcriptional activity of nuclear hormone receptors and other transcription factors (Sharma, et al. (2003) *EMBO J.* 22:6101-6114; Beliakoff & Sun (2006) *Nucl. Recept. Signal* 4:e017; Li, et al. (2006) *J. Biol. Chem.* 281:23748-56). An ortholog of Zmiz1, called tonalli (tna), has been identified in *Drosophila* and genetically interacts with the ATP-dependent SWI/SNF and Mediator complexes (Gutierrez, et al. (2003) *Development* 130:343-354). In addition, an interaction between the Zmiz1 and Notch1 pathways has been implicated in promoting c-MYC activity in acute T lymphoblastic leukemia (Rakowski, et al. (2013) *Cancer Res.* 73:930-941). However, the function of Zmiz1 in the inner ear of humans has not been described.

Myt1 binds to the promoter regions of proteolipid proteins of the central nervous system and plays a role in the developing nervous system. Myt1 has been shown to be useful in reprogramming mouse embryonic fibroblasts into neurons (Vierbuchen, et al. (2010) *Nature* 463:1035-1041). However, the function of Myt1 in the inner ear of humans has not been described.

Stat3 plays a role in cellular oxidative stress injury, as inhibition of JAK2/Stat3 signaling activity reduces hydrogen peroxide-induced cell death (Duan, et al. (2013) *PLoS ONE* 8:e57941; Yu, et al. (2006) *Apoptosis* 11:931-41; Ponnusamy, et al. (2009) *Am. J. Physiol. Renal Physiol.* 297:F1361-70). Several Stat3 target genes, including IL-6, MCP1 and NOX1 and NOX4, are up-regulated by loud sound and are involved in the ensuing cochlear tissue damage and loss of hearing sensitivity (Vlajkovic, et al. (2013) *Hear. Res.* 304:145-52; Tornabene, et al. (2006) *Hear. Res.* 222:115-124; Wakabayashi, et al. (2010) *Neurosci. Res.* 66:345-52). Further, it has been demonstrated that inhibiting the Stat3 signaling pathway reduces OHC loss and improves auditory sensitivity following loud sound exposure (Wilson, et al. (2014) *PLoS ONE* 9(10):e108276). Moreover, Stat3 inhibition has been suggested to stimulate hair cell regeneration (Liang, et al. (2012) *J. Neurosci.* 32(31):10662-73).

Barhl1 is expressed by developing inner ear hair cells, cerebellar granule cells, precerebellar neurons, and collicular neurons. Targeted gene inactivation has demonstrated a crucial role for Barhl1 in the survival and/or migration of these sensory cells and neurons (Li, et al. (2004) *J. Neurosci.* 24:3104-3114; Li & Xiang (2006) *Dev. Dyn.* 235:2260-2265). Further, it has been shown that Atoh1 is required for proper Barhl expression in the inner ear and CNS (Chellappa, et al. (2008) *Mol. Cell Biol.* 28(6):1905-1914; Chonko, et al. (2013) *Dev. Biol.* 381:401-10).

Tox is dynamically regulated in T cell development with peak expression occurring when thymocytes are actively undergoing T cell receptor recombination. Tox is best known for regulating the specification of the mature CD4+ T cells (Wilkinson, et al. (2002) *Nat. Immunol.* 23(3):272-280). However, the function of Tox in the inner ear of humans has not been described.

Rfx7 and Rfx3 have been described as being expressed in HCs (Elkon, et al. (2015) *Nat. Commun.* 6:8549). However, the function of Rfx7 in the inner ear of humans has not been described.

Prox1 is expressed in the otocyst beginning at embryonic day 11, in the developing vestibular sensory patches. Expression is down-regulated in maturing (myosin VIIA immunoreactive) vestibular hair cells and subsequently in the underlying support cell layer by E16.5. Prox1 becomes restricted to a subset of supporting cells. Double labeling for Prox1 and cell-type specific markers reveals that the outer hair cells transiently express Prox1. After E18, Prox1 protein is no longer detectable in hair cells, but it continues to be expressed in supporting cells for the rest of embryogenesis and into the second postnatal week. Prox1 is not expressed in all supporting cell types in the organ of Corti, but is restricted to developing Deiters' and pillar cells (Bermingham-McDonogh, et al. (2006) *J. Comp. Neurol.* 496(2):172-86). It has been suggested that Prox1 antagonizes the hair cell phenotype in these non-sensory cells (Kirjavainen, et al. (2008) *Dev. Biol.* 322:33-45). In this respect, siRNA targeting Prox1 to increase expression of Atoh1 in human adult cochlear supporting cells has been suggested for use in hearing enhancement (US 2012/0207744).

Lying downstream of Notch signaling and Sox1, Nfia has been suggested to be necessary for the maintenance of Notch-induced Hes5 expression, while it can also downregulate Dll1, Ngn2, Hes1 and Hes5 under different circumstances (Su, et al. (2015) *Gene* 558:6-24). However, the function of Nfia in the inner ear of humans has not been described.

Thrb is a nuclear hormone receptor for triiodothyronine. Thrb has been shown to be essential for normal development of the mammalian auditory system. In particular, Thrb mutations leading to loss of triiodothyronine binding result in abnormal hair cell function and sensorineural hearing impairment (Griffith, et al. (2002) *JARO* 3:279-88; Ng, et al. (2015) *Endocrinology* 156:3853-65; WO 1996/035785). However, overexpression of Thrb in the inner ear of humans has not been described.

Expression of Mycl1 is restricted to brain, kidney and inner ear (Pirity, et al. (2006) *Curr. Top. Microbiol. Immunol.* 302:205-34). In contrast to N-Myc and C-Myc null mice, L-Myc null mice are viable without a noticeable phenotype; however, L-Myc is always co-expressed with either of the two other Mycs (Hatton, et al. (1996) *Mol. Cell Biol.* 16:1794-1804). Loss of L-Myc results in some auditory and vestibulo-motor abnormalities (Kopecky, et al. (2013) *Dev. Dyn.* 242:132-147). In this respect, regeneration of inner ear sensory epithelium by exogenous expression of L-Myc and/or Atoh1 has been described (WO 2013/134022).

Missense mutations in the H3K4 demethylase Kdm5a/ Jarid1a have been linked to an autosomal recessive form of intellectual disability (Najmabadi, et al. (2011) *Nature* 478:

57-63). However, the function of Kdm5a in the inner ear of humans has not been described.

Bach2 encodes a transcriptional repressor of B cells (Sasaki, et al. (2000) *Oncogene* 19:3739-3749), which is a key regulator of CD4(+) T-cell differentiation that prevents inflammatory disease by controlling the balance between tolerance and immunity. Genetic polymorphisms analysis shows that Bach2 is associated with asthma, Crohn's disease, multiple sclerosis and T1D (Roychoudhuri, et al. (2013) *Nature* 498:506-510). Bach2 is upregulated in noise-exposed *cochleae* compared to the normal *cochleae* (Patel, et al. (2013) *PLoS ONE* 8(3):e58471) and the use of siRNA to inhibit the expression of Bach2 and prevent or attenuate otopathologies have been described (U.S. Pat. No. 7,825,099). However, overexpression of Bach2 in the inner ear of humans has not been described.

Creb314 (also called AIbZIP, Tisp40, or ATCE1) is expressed in human prostate tissue (Fujii, et al. (2002) *EMBO Rep.* 3:367-372), and Creb314 disruption resulted in abnormal epididymal sperm nuclei, ER stress, and activation of caspase 12, leading to apoptosis of meiotic/postmeiotic germ cells (Nagamori, et al. (2006) *Genes Cells* 11:1161-71). However, the function of Creb314 in the inner ear of humans has not been described.

Etv1 is expressed in utricle sensory epithelia (Hawkins, et al. (2003) *Hum. Mol. Genet.* 12:1261-72). However, the function of Etv1 in the inner ear of humans has not been described.

Isl1 has been suggested to play a role in hearing loss. In particular, transgenic animals expressing Isl1 have been found to be less susceptible to age-related hearing loss (ARHL) and noise-induced hearing loss (NIHL). See U.S. Pat. No. 9,149,024. However, Isl1 has not been suggested to be a co-transcription factor to Atoh1 for hair cell regeneration. Antibodies that can be used to detect an Isl1 polypeptide are commercially available, e.g., from Cell Signaling Technology, Abeam, Novus Biologicals, Sigma-Aldrich, R&D Systems, Millipore, Abnova, and/or Invitrogen).

Zbtb38 has been associated with adult height in different populations (Wang, et al. (2013) *Clin. Endocrinol.* 79:402-8). However, the function of Zbtb38 in the inner ear of humans has not been described.

Lbh expression has been shown to be differentially expressed in OHCs (Liu, et al. (2014) *J. Neurosci.* 34:11085-95; Li, et al. (2016) *PLoS ONE* 11:e0151291). In addition, a significant increase of Lbh expression in both cochlear and vestibular HCs has also been detected between E18 and P7 (Scheffer, et al. (2015) *J. Neurosci.* 35:6366-6380). However, the function of Lbh in the inner ear of humans has not been described.

In mouse embryos, Tub is expressed selectively in differentiating neurons of the central and peripheral nervous systems, starting at 9.5 days after conception. In adult mice, Tub is transcribed in several major brain areas, including cerebral cortex, hippocampus, several nuclei of the hypothalamus controlling feeding behavior, in the spiral ganglion of the inner ear, and in photoreceptor cells of the retina (Sahly, et al. (1998) *Hum. Molec. Genet.* 7:1437-1447). Tub$^{-/-}$ mice (Coleman & Eicher (1990) *J. Hered.* 81:424) exhibit progressive sensorineural degeneration of the retina and cochlear hair cells (Ohlemiller, et al. (1995) *Neuroreport.* 6:845; Heckenlively, et al. (1995) *Proc. Natl Acad. Sci. USA* 92:11100-11104). However, overexpression of Tub in the inner ear of humans has not been described.

Hmg20a, also known as iBraf, is a chromatin remodeling factor implicated in the relief of transcriptional repression induced by the LSD1-CoREST complex. Hmg20a is expressed in pancreatic islets and HC (Hickox, et al. (2016) *J. Neurosci.* 37:1320-1339), and mutations in this gene have been associated with T2DM (Mellado-Gil, et al. (2016) *Diabetologia* 59:S194). However, the function of Hmg20a in the inner ear of humans has not been described.

Rest, also known as Nrsf (neuron-restrictive silencer factor), is a transcriptional repressor of neural genes. Rest null mice have embryonic lethality which prevents further investigations of the functions of the Rest gene in vivo. Rest conditional knockout mice indicate a failure of gut function by underdeveloped cholinergic transmission in the enteric nervous system (Aoki, et al. (2014) *Gene Cells* 19:723-42). Further, constitutive expression of Rest in differentiating neurons disrupts neuronal gene expression and causes axon pathfinding errors in vivo (Paquette, et al. (2000) *Proc. Natl. Acad. Sci. USA* 97:12318-12323). However, the function of Rest in the inner ear of humans has not been described.

Zfp827 is a known transcription factor. However, the function of Zfp827 in the inner ear of humans has not been described.

Aff3 is preferentially expressed in lymphoid tissue. Aff3 has been suggested for use in enhancing tissue or organ regeneration, e.g., in the treatment of hearing loss (WO 2014/197421). However, co-expression of Aff3 with Atoh1 in the inner ear of humans has not been described.

Pknox2 is expressed by HC (Hickox, et al. (2016) *J. Neurosci.* 37:1320-1339). However, the function of Pknox2 in the inner ear of humans has not been described.

Arid3b is highly expressed in the pharyngeal arches and their derivatives of craniofacial microsomia-related craniofacial substructures, such as jaw, ear and eye as determined by in situ hybridization in the embryos of mouse, chicken and frog (Zhang, et al. (2016) *Nat. Commun.* 7:10605). However, the function of Arid3b in the inner ear of humans has not been described.

Mlxip forms heterodimers with Mlx that can bind to and activate transcription from CACGTG E boxes. However, the function of Mlxip in the inner ear of humans has not been described.

Zfp532 is a known transcription factor. However, the function of Zfp532 in the inner ear of humans has not been described.

Ikzf2 is expressed by OHC (Li, et al. (2016) *PLoS ONE* 11:e0151291). In vitro analyses demonstrate that mutant Ikzf2 can localize to the nucleus, but has an impaired ability to homodimerize—a prerequisite for DNA binding. In both Ikzf2$^{+/+}$ and Ikzf2$^{cello/cello}$ cochleae, hellos is expressed in the nuclei of the OHCs from the first postnatal week and at P16 Ikzf2$^{cello/cello}$ exhibit severely impaired hearing. It has been suggested that Ikzf2 has a key role in regulating the maturing OHC transcriptome (Chessum (2015) *Ph.D. Thesis, University of* Oxford). However, overexpression of Ikzf2 in the inner ear of humans has not been described.

Sall1 is expressed in supporting cells at P1 and P6 (Maass (2016) *PLoS ONE* 11(12):e0167286). Mutations in Sall1 have been identified as being responsible for Townes-Brocks syndrome (TBS), an autosomal dominantly inherited malformation syndrome characterized by ear malformations with sensorineural hearing loss (Liang, et al. (2008) *J. Pediatr. Surg.* 43(2):391-3). However, co-expression of Sall1 and Atoh1 in the inner ear of humans has not been described.

Six2 is upregulated in ear progenitor cells following exposure to c-myc and NICD (US 2015/0209406). In addition, Six2 haploinsufficiency has been suggested as a potential congenital factor attributed to developmental malformation of the middle ear ossicles and upper eyelid (Guan, et al.

(2016) *J. Hum. Genet.* 61:917-22). However, overexpression of Six2 in the inner ear of humans has not been described.

Sall3 is normally highly expressed in the inner ear, in the dorsal horn of the spinal cord, and in some motor neurons of the ventral horn. Sall3-deficient animals exhibit malformations of the palate, epiglottis, and tongue, all of which may inhibit normal feeding behavior (Parrish, et al. (2004) *Mol. Cell Biol.* 24(16):7102-7112). However, co-expression of Sall3 and Atoh1 in the inner ear of humans has not been described.

In humans and mice, Lin28b is a critical regulator of stemness, organismal growth, metabolism, tumorigenesis, and tissue repair. Using iLIN28B and flet-7 g transgenic mouse lines (Zhu, et al. (2011) *Cell* 147(1):81-94), it has been shown that Lin28b functions as a developmental timer in the murine cochlea through both let-7-dependent and let-7-independent mechanisms. Furthermore, reexpression of Lin28b enhances the ability of early postnatal SCs to switch cell fate and transdifferentiate into HCs in response to Notch inhibition (Golden, et al. (2015) *Proc. Natl. Acad. Sci. USA* 112:E3864-73). However, co-expression of Lin28b and Atoh1 in the inner ear of humans has not been described.

Missense mutations in Pou4f3 cause autosomal dominant hearing impairment (Collin, et al. (2008) *Hum. Mutat.* 29(4):545-54. In this respect, the use Atoh1 and Pou4f3 for turning on a maturation pathway in hair cells and treating an otic disease has been suggested (WO 2015/048577; WO/2014/145205; US 2015/0050354; Walters, et al. (2017) *Cell Reports* 19:307-320).

Peg3 is an imprinted gene expressed exclusively from the paternal allele and plays important roles in controlling fetal growth rates and nurturing behaviors as has potential roles in mammalian reproduction (Kim, et al. (2013) *PLoS ONE* 8(12):e83359). Microarray analysis comparing the expression pattern of the developing superior olivary complex (SOC) with that of the entire brain revealed increased expression of Peg3 in the SOC before (P4) and after (P25) hearing onset, compared to the entire brain (Ehmann, et al. (2013) *J. Biol. Chem.* 288:25865-79). However, co-expression of Peg3 and Atoh1 in the inner ear of humans has not been described.

Rorb is an orphan nuclear receptor, forming a subfamily with the closely related nuclear receptors ROR-alpha. Rorb$^{-/-}$ mice are blind, yet their circadian activity rhythm is still entrained by light-dark cycles (Andre, et al. (1998) *Gene* 216:277-283). However, the function of Rorb in the inner ear of humans has not been described.

To promote the differentiation of non-sensory cells of the sensory epithelium, i.e., supporting cells, into sensory hair cells, Atoh1 (a Group 2 transcription factor) can be co-expressed with a co-transcription factor from Group 1, Group 2, Group 3 and/or Group 4 as presented in Table 1. In some embodiments, the co-transcription factor is Sox9, Sall2, Camta1, Hey2, Gata2, Hey1, Lass2, Sox10, Gata3, Cux1, Nr2f1, Hes1, Rorb and/or Jun. In other embodiments, the co-transcription factor is Zfp667, Lhx3, Nhlh1, Mdx4, Zmiz1, Myt1, Stat3, Barhl1, Tox, Prox1, Nfia, Thrb, Mycl1, Kdm5a, Creb314, Etv1, Peg3 and/or Bach2. In still further embodiments, the co-transcription factor is Lin28b, Pou4f3 and/or Rfx7. Ideally, Atoh1 is co-expressed with one or more Group 3 co-transcription factors. In particular, Atoh1 is co-expressed with one or more of Isl1, Zbtb38, Lbh, Tub, Hmg20, Rest, Zfp827, Aff3, Pknox2, Arid3b, Mlxip, Zfp532, Ikzf2, Sall1, Six2 and/or Sall3. Preferably, Atoh1 is co-expressed with one or more Isl1, Zbtb38, Tub, Zfp827, Aff3, Mlxip and Zfp532. In an alternative aspect of this invention, the co-transcription factor is not Sox9, Hey2, Gata2, Hey1, Gata3, Cux1, Mxd4, Hes1, Jun, Lhx3, Stat3, Prox1, Mycl1, Bach2 and/or Pou4f3.

In some embodiments, the co-transcription factor is Isl1. As used herein, "Isl1" refers to any and all Isl1-associated nucleic acid or protein sequences and includes any sequence that is orthologous or homologous to, or has significant sequence similarity to, an Isl1 nucleic acid or amino acid sequence derived from any animal including mammals (e.g., humans) and insects. Isl1 also includes all other synonyms that may be used to refer to this gene or the protein product of this gene (synonyms for this gene include ISL LIM homeobox 1, ISL1 transcription factor, LIM/homeodomain 2, ISL1 transcription factor, LIM/homeodomain, and islet-1).

Gene Silencing Complexes.

As used herein, a "gene silencing complex" refers to complex of proteins that epigenetically modulate gene expression via chromatin remodeling, e.g., by methylation/demethylation or acetylation/deacetylation. It has been shown that cofactors of the nucleosome remodeling and deacetylation (NuRD) and polycomb repressive complex 2 (PRC2) repressive complexes are present in the neonatal organ of Corti (Layman, et al. (2013) *Hear Res.* 304:167-178). By P6, these NuRD cofactors are mostly undetectable by immunofluorescence and completely lost by P7, but are detectable again at P8 and continue to be present through P21. The PRC2 enzymatic subunit, EZH2 is also highly present from E18.5 to P0 in the organ of Corti, but lost between P2 and P4. However, EZH2 staining is evident again throughout the organ of Corti by P6 and persists through P21. Accordingly, in certain embodiments of this invention, an inhibitor targeting one or more subunits of the NuRD or PRC2 complex is used.

The NuRD complex is a transcriptional co-repressor essential for developmental transitions. The NuRD complex is a multi-protein complex containing both histone deacetylase (HDAC1/2) and chromatin remodeling ATPase (Mi2) polypeptides, as well as a number of others. NuRD has been shown to interact with a number of transcription factors, and analyses of mice bearing targeted mutations of NuRD subunits have revealed their important roles in various aspects of development, including a role for Mi2beta in self-renewal and multilineage differentiation of hematopoietic stem cells. MTA1, the signature subunit of NuRD, was previously shown to directly interact with the estrogen receptor (ER) and to act as a co-repressor of ER-mediated transcriptional repression. For a review of the NuRD complex, see, for example, Ramirez, et al. (2009) *Epigenetics* 4:532-6 and Yang, et al. (2008) *Nat. Rev. Mol. Cell. Biol.* 9:206-18.

Representative amino acid sequences of polypeptides involved in the NuRD complex include, for example, GEN-BANK Accession Nos. NP_004955.2 (HDAC1), NP_001518.3 (HDAC2), NP_001264 (Mi2beta), and NP_004680 (MTA1). Lysine-specific histone demethylase 1 (KDM1A or Lsd1), is also associated with the NuRD complex to demethylate di- and tri-methylated histone H3K4 (Wang, et al. (2009) *Cell* 138:660-672). Representative amino acid sequences for Lsd1 are found under GEN-BANK Accession Nos. NP_001009999 and NP_055828.

PRC2 is a transcriptional repressor complex required for gene silencing during multiple developmental processes. The PRC2 core, conserved from *Drosophila* to humans, is composed of four proteins that add up to about 230 kDa: EED (Embryonic Ectoderm Development; present in different isoforms), either one of the two methyltransferases Ezh1 or Ezh2 (Enhancer of Zeste Homolog 1/2), Suz12 (Suppressor of Zeste 12), and either RbAp46 or RbAp48 (RbAp46/ 48). There are additional homologs and variants of these proteins that are reviewed elsewhere (see, e.g., Di Croce and Helin (2013) *Nat. Struct. Mol. Biol.* 20:1147-55).

Both Ezh1 and Ezh2 contain enzymatic methyltransferase activity within a C-terminal SET (Su(var)3-9, Enhancer-of-zeste, Trithorax) domain. PRC2 complexes containing Ezh1 have lower enzymatic activity than those containing Ezh2, and target a subset of Ezh2 genes. Ezh2 activity appears to depend on interaction with both Suz12 and the WD40 domain in EED. EED's WD40 beta propeller, in turn, interacts with H3K27me3 repressive marks. This interaction is proposed to promote the allosteric activation of PRC2 methyltransferase activity. RbAp48 also contains a WD40 propeller required for interaction with both Suz12 and the first 10 residues of unmodified Histone H3 peptides.

Human EED, Ezh1, Ezh2, Suz12, RbAp46 and RbAp48 nucleic acids and polypeptides have previously been described. For example, nucleic acids and polypeptides for EED are provided under GENBANK Accession Nos. NM_003788 and NP_003788 (isoform a); NM_001308007 and NP_001294936 (isoform c); and NM_001330334 and NP_001317263 (isoform d). See also, e.g., Chen, et al. (1996) *Genomics* 38:30-7; Swiss-Prot Accession No. Q15910; GENBANK Accession Nos. NM_004456 and NP_004447 (isoform a); and GENBANK Accession Nos. NM_152998 and NP_694543 (isoform b) for Ezh1 nucleic acids and polypeptide. See, e.g., GENBANK Accession Nos. NM_001991 and NP_001982 (isoform 1); NM_001321079 and NP_001308008 (isoform 2); NM_001321082 and NP_001308011 (isoform 3); and NM_001321081 and NP_001308010 (isoform 4) for Ezh2 nucleic acids and polypeptides.

Inhibitors of Gene Silencing Complexes.

An inhibitor of a gene silencing complex is intended to refer to any molecule that reduced, blocks or decreases the expression or activity of a subunit of a gene silencing complex, e.g. PRC2 or NuRD. In this respect, the inhibitor of this invention can be a nucleic acid-based inhibitor such as an inhibitory RNA molecule (e.g., antisense molecule, a ribozyme, siRNA, miRNA, etc.); a protein that affects splicing or 3' processing (e.g., polyadenylation), or a protein that affects the level of expression of another gene within the cell (i.e., where gene expression is broadly considered to include all steps from initiation of transcription through production of a process protein), such as by mediating an altered rate of mRNA accumulation or transport or an alteration in post-transcriptional regulation; peptides or a small organic molecule; as well as genome editing including CRISPRs, zinc fingers, and tale nucleases to knock-out or knock-down a gene.

When the inhibitor is, e.g., an inhibitory RNA, peptide or protein (including gene editing enzymes), nucleic acid molecules encoding such an inhibitor can be carried by the same nucleic acid molecule that encodes the atonal-associated factor and/or co-transcription factor or can be a separate nucleic acid molecule present on the same expression vector or part of a different expression vector. Inhibitory RNA molecules can be readily prepared based upon the nucleic acid sequences disclosed herein. Alternatively, inhibitory RNA molecules such as siRNAs can be obtained from commercial sources such as Dharmacon, Invitrogen or Zyagen. Exemplary peptide inhibitors of PRC2 include, e.g., those disclosed in U.S. Pat. No. 9,388,213, incorporated herein by reference in its entirety.

Small organic molecules as inhibitors of gene silencing complexes are also known in the art. For example, HDAC inhibitors include non-peptide hydroxamic acid inhibitors (see, e.g., WO 1997/35990, U.S. Pat. Nos. 5,369,108, 5,608, 108, 5,700,811, WO 2001/18171, WO 1998/55449, WO 1993/12075, WO 2001/49290, WO 2002/26696, WO 2002/ 26703, WO 1999/12884, WO 2001/38322, WO 2001/70675 and WO 2002/22577); cyclic peptide inhibitors (see, e.g., U.S. Pat. Nos. 5,620,953, 5,922,837, WO 2001/07042, WO 2000/08048, WO 2000/21979, WO 1999/11659, and WO 2000/52033); inhibitors based on a benzamide structure (see, e.g., U.S. Pat. No. 6,174,905, JP 11269140, JP 11335375, JP 11269146, WO 2001/38322, WO 2001/70675 and WO 2001/34131); butyric acid analogues (see e.g., WO 1999/37150, EP 1170008, WO 2002/07722, WO 1998/ 00127, WO 1998/39965, WO 1998/39966, WO 1998/40066, WO 1998/40065 and WO 1998/40080); and electrophilic ketone inhibitors (see, e.g., WO 2001/18171 and WO 2002/ 46129).

Similarly, Lsd1 inhibitors include, but are not limited to, trans-2-phenyl-cyclopropylamine (tranylcypromine) and its derivatives (see, e.g., Hojfeldt, et al. (2013) *Nat. Rev. Drug Discovery* 12:917-30); propargylamine derivatives (see, e.g., Culhane, et al. (2006) *J. Am. Chem. Soc.* 128:4536-7) and cyclopropylamine derivatives (see, e.g., U.S. Pat. No. 8,853,408).

Inhibitors of EED include the protein-protein interaction inhibitor A-395 (He, et al. (2017) *Nat. Chem. Biol.* doi: 10.1038/nchembio.2306); and EED226, a potent and selective PRC2 inhibitor that directly binds to the H3K27me3 binding pocket of EED (Qi, et al. (2017) *Nat. Chem. Biol.* doi:10.1038/nchembio.2304);

Molecules that inhibit the activity of one or both of EZH1/2, include but not limited, to DS-3201 (Daiichi Sankyo Inc), UNC1999 (Xu, et al. (2015) *Blood* 125(2):346-57) and ZLD1122 (Gao, et al. (2016) *RSC Adv.* 6:28512-21) as well as those disclosed in Garapaty-Rao, et al. (2013) *Cell Chem. Biol.* 20(11):1329-39.

Inhibition may also be achieved by gene editing to inhibit expression of the gene at the genomic level, e.g., gene knock-out via, for example, deletion or mutation of a subunit of a gene silencing complex. As used herein, a "knock-out" can be a gene knockdown or the gene can be knocked out by a mutation such as, a point mutation, an insertion, a deletion, a frameshift, or a missense mutation by techniques known in the art, including, but not limited to, retroviral gene transfer. In certain embodiments, gene editing refers to a zinc-finger nuclease (ZFN), transcription activator-like effector nuclease (TALEN) or CRISPR/Cas9. Zinc-finger nucleases are artificial restriction enzymes generated by fusing a zinc finger DNA-binding domain to a DNA-cleavage domain. Zinc finger domains can be engineered to target desired DNA sequences, which enable zinc-finger nucleases to target unique sequence within a complex genome. By taking advantage of endogenous DNA repair machinery, these reagents can be used to precisely alter the genomes of higher organisms. Other technologies for genome customization that can be used to knock out genes are meganucleases and TALENs. A TALEN is composed of a TALE DNA binding domain for sequence-specific recognition fused to the catalytic domain of an endonuclease that introduces double strand breaks (DSB). The DNA binding domain of a TALEN is capable of targeting with high precision a large recognition site (for instance 17 bp). Meganucleases are sequence-specific endonucleases, naturally occurring "DNA scissors," originating from a variety of single-celled organisms such as bacteria, yeast, algae and some plant organelles. Meganucleases have long recognition sites of between 12 and 30 base pairs. The recognition site of natural meganucleases can be modified in order to target native genomic DNA sequences (such as endogenous genes). Another genome editing technology is the CRISPR/Cas system, which can be used to achieve RNA-guided genome engineering. CRISPR interference is a genetic technique which allows for sequence-specific control of gene expression in prokaryotic and eukaryotic cells. It is based on the bacterial immune system-derived CRISPR (clustered regularly interspaced palindromic repeats) pathway.

Sensory Perception.

In particular, the invention provides a method of improving the sensory perception of an animal. The method includes administering to the inner ear an expression vector (e.g., expression viral vector) harboring a nucleic acid molecule encoding an atonal-associated factor in combination with a co-transcription factor and/or inhibitor of a gene silencing complex (e.g., an inhibitor of the PRC2 or NuRD complex). The nucleic acid molecule is expressed to produce the atonal-associated factor, which results in generation of sensory hair cells that allow perception (or recognition) of stimuli in the inner ear. The combination of the nucleic acid molecule encoding an atonal-associated factor and the co-transcription factor and/or inhibitor of a gene silencing complex increases in reprogramming efficiency and/or terminal differentiation of some reprogrammed cells. By "change of sensory perception" is meant achieving, at least in part, the ability to recognize and adapt to environmental changes. In terms of sensory hair cell function, a change in sensory perception is associated with the generation of sensory hair cells that convert mechanical stimuli in the inner ear into neural impulses, which are then processed in the brain such that an animal is aware of environmental change, e.g., sound, language, or body/head position. Sensory hair cells are preferably generated in the organ of Corti and/or vestibular apparatus.

Sensory hair cell generation can be determined using a variety of means, such as those known to one skilled in the art. Hair cells can be detected via scanning electron microscopy and/or via detection of myosin VIIa, a hair cell-specific protein detected by immunochemistry. However, the mere presence of sensory hair cells does not necessarily imply a functional system for recognizing environmental stimuli. Functional sensory hair cells must be operably linked to neural pathways, such that mechanical stimuli are translated to nerve impulses recognized by the brain. Accordingly, while detection of hair cell generation is appropriate for determining successful expression of the atonal-associated nucleic acid sequence to target tissue, examination of subject awareness is a more desirable indicator of changes in sensory perception.

A change in the ability of a subject to detect sound is readily accomplished through administration of simple hearing tests, such as a tone test commonly administered by an audiologist. In most mammals, a reaction to different frequencies indicates a change in sensory perception. In humans, comprehension of language also is appropriate. For example, it is possible for a subject to hear while being unable understand speech. A change in perception is indicated by the ability to distinguish different types of acoustic stimuli, such as differentiating language from background noise, and by understanding speech. Speech threshold and discrimination tests are useful for such evaluations.

Evaluation of changes in balance, motion awareness, and/or timing of response to motion stimuli also is achieved using a variety of techniques. Vestibular function also can be measured by comparing the magnitude of response to motion stimulus (gain) or timing of initiation of response (phase). Animals can be tested for Vestibulo-Ocular Reflex (VOR) gain and phase using scleral search coils to evaluate improvements in sensory perception. Electronystagmography (ENG) records eye movements in response to stimuli such as, for instance, moving or flashing lights, body repositioning, fluid movement inside the semicircular canals, and the like. Evaluation of balance during movement using a rotating chair or moving platform also is useful in this respect.

To detect an improvement in sensory perception, a baseline value is recorded prior to the inventive method using any appropriate sensory test. A subject is reevaluated at an appropriate time period following the inventive method (e.g., 1 hour, 6 hours, 12 hours, 18 hours, 1 day, 3 days, 5 days, 7 days, 14 days, 21 days, 28 days, 2 months, 3 months or more following the inventive method), the results of which are compared to baseline results to determine an improvement in sensory perception.

Method of Treatment.

The inventive method promotes the generation of sensory hair cells that allow perception of stimuli. Accordingly, this invention also provides a method for treating hearing loss by administering to the inner ear of a subject in need of treatment an expression vector (e.g., expression viral vector) harboring a nucleic acid molecule encoding an atonal-associated factor in combination with a co-transcription factor and/or inhibitor of a gene silencing complex (e.g., an inhibitor of the PRC2 or NuRD complex). Ideally, the inventive method prophylactically or therapeutically treats an animal for at least one disorder associated with loss, damage, absence of sensory hair cells, such as hearing loss and balance disorders. Hearing loss can be caused by damage of hair cells of the organ of Corti due to bacterial or viral infection, heredity, physical injury, acoustic trauma, and the like. While hearing loss is easily identified, balance disorders manifest in a broad variety of complications easily attributable to other ailments. Symptoms of a balance disorder include disorientation, dizziness, vertigo, nausea, blurred vision, clumsiness, and frequent falls. Balance disorders treated by the inventive method preferably involve a peripheral vestibular disorder (i.e., a disturbance in the vestibular apparatus) involving dysfunctional translation of mechanical stimuli into neural impulses due to damage or lack of sensory hair cells.

By "prophylactic" is meant the protection, in whole or in part, against a disorder associated with dysfunctional (or absence of) hair cells, in particular hearing loss or a balance disorder. By "therapeutic" is meant the amelioration of the disorder, itself, and desirably the protection, in whole or in part, against further progression of the disease, e.g., progressive hearing loss. One of ordinary skill in the art will appreciate that any degree of protection from, or amelioration of a disorder such as hearing loss or balance disruption is beneficial to a patient.

The method is useful in the treatment of both acute and persistent, progressive disorders associated with lack of or damage to functional sensory hair cells. For acute ailments, the combination of the expression vector and co-transcription factor and/or inhibitor of a gene silencing complex can be administered using a single application or multiple applications within a short time period. For persistent diseases, such as hearing loss, or disorders stemming from a massive loss of sensory hair cells, numerous rounds of administration of the expression vector and co-transcription factor and/or inhibitor of a gene silencing complex may be necessary to realize a therapeutic effect.

Expression Vectors.

One of ordinary skill in the art will appreciate that any of a number of expression vectors known in the art are suitable for introducing the nucleic acid sequence to the inner ear. Examples of suitable expression vectors include, for instance, plasmids, plasmid-liposome complexes, and viral vectors, e.g., parvoviral-based vectors (i.e., adeno-associated virus (AAV)-based vectors), retroviral vectors, herpes simplex virus (HSV)-based vectors, AAV-adenoviral chimeric vectors, and adenovirus-based vectors. Any of these expression vectors can be prepared using standard recombinant DNA techniques described in, e.g., Sambrook, et al. (1989) *Molecular Cloning, A Laboratory Manual*, 2$^{nd}$ Ed., Cold Spring Harbor Press, Cold Spring Harbor, N.Y.; and Ausubel, et al. (1994) *Current Protocols in Molecular Biology, Greene Publishing Associates and* John Wiley & Sons, New York, N.Y.

Plasmids, genetically engineered circular double-stranded DNA molecules, can be designed to contain an expression cassette for delivery of a nucleic acid sequence to the inner ear. Although plasmids were the first vector described for the administration of therapeutic nucleic acids, the level of transfection efficiency is poor compared with other techniques. By complexing the plasmid with liposomes, the efficiency of gene transfer in general is improved. While the liposomes used for plasmid-mediated gene transfer strategies have various compositions, they are typically synthetic cationic lipids. Advantages of plasmid-liposome complexes include their ability to transfer large pieces of DNA encoding a therapeutic nucleic acid and their relatively low immunogenicity. Plasmids also can be modified to prolong transgene expression as described in U.S. Pat. No. 6,165,754. Expression of a transgene in the ear using plasmids has been described (see, for example, Jero, et al. (2001) *Human Gene Ther.* 12:539-549). While plasmids are suitable for use in the inventive method, preferably the expression vector is a viral vector.

AAV vectors are viral vectors of particular interest for use in gene therapy protocols. AAV is a DNA virus, which is not known to cause human disease. AAV requires co-infection with a helper virus (i.e., an adenovirus or a herpes virus), or expression of helper genes, for efficient replication. AAV vectors used for administration of a therapeutic nucleic acid have approximately 96% of the parental genome deleted, such that only the terminal repeats (ITRs), which contain recognition signals for DNA replication and packaging, remain. This eliminates immunologic or toxic side effects due to expression of viral genes. Host cells containing an integrated AAV genome show no change in cell growth or morphology (see, for example, U.S. Pat. No. 4,797,368). Although efficient, the need for helper virus or helper genes can be an obstacle for widespread use of this vector.

Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. When employing pathogenic retroviruses, e.g., human immunodeficiency virus (HIV) or human T-cell lymphotrophic viruses (HTLV), care must be taken in altering the viral genome to eliminate toxicity. A retroviral vector can additionally be manipulated to render the virus replication-incompetent. As such, retroviral vectors are thought to be particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, are particularly useful in the sensory epithelium of the inner ear where sensory cells do not regenerate.

HSV-based viral vectors are suitable for use as an expression vector to introduce nucleic acids into the inner ear for transduction of target cells. The mature HSV virion is composed of an enveloped icosahedral capsid with a viral genome composed of a linear double-stranded DNA molecule that is 152 kb. Most replication-deficient HSV vectors contain a deletion to remove one or more intermediate-early genes to prevent replication. Advantages of the herpes vector are its ability to enter a latent stage that can result in long-term DNA expression, and its large viral DNA genome that can accommodate exogenous DNA up to 25 kb. Of course, this ability is also a disadvantage in terms of short-term treatment regimens. For a description of HSV-based vectors appropriate for use in the inventive methods, see, for example, U.S. Pat. Nos. 5,837,532, 5,846,782, 5,849,572, 5,804,413, WO 1991/02788, WO 1996/04394, WO 1998/15637, and WO 1999/06583.

Adenovirus (Ad) is a 36-kb double-stranded DNA virus that efficiently transfers DNA in vivo to a variety of different target cell types. For use in the inventive method, the virus is preferably made replication-deficient by deleting select genes required for viral replication. The expendable non-replication-essential E3 region is also frequently deleted to allow additional room for a larger DNA insert. The vector can be produced in high titers and can efficiently transfer DNA to replicating and non-replicating cells. Genetic information transferred to a cell by way of an adenoviral vector remains epi-chromosomal, thus eliminating the risks of random insertional mutagenesis and permanent alteration of the genotype of the target cell. However, if desired, the integrative properties of AAV can be conferred to adenovirus by constructing an AAV-Ad chimeric vector. For example, the AAV inverted terminal repeats (ITRs) and nucleic acid encoding the Rep protein incorporated into an adenoviral vector enables the adenoviral vector to integrate into a mammalian cell genome. Therefore, AAV-Ad chimeric vectors are an interesting option for use in the context of the invention.

Preferably, the expression vector of the inventive method is a viral vector; more preferably, the expression vector is an adenoviral vector. Adenovirus from any origin, any subtype, mixture of subtypes, or any chimeric adenovirus can be used as the source of the viral genome for the adenoviral vector of the invention. A human adenovirus preferably is used as the source of the viral genome for the replication-deficient adenoviral vector. The adenovirus can be of any subgroup or serotype. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 are available from the American Type Culture Collection (ATCC, Manassas, Va.). Preferably, the adenoviral vector is of subgroup C, especially serotype 2 or even more desirably serotype 5.

However, non-group C adenoviruses, and even non-human adenoviruses, can be used to prepare replication-deficient adenoviral gene transfer vectors for delivery of DNA to target cells in the inner ear. Preferred adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, 5,849,561, WO 1997/12986 and WO 1998/53087. Preferred non-human adenoviruses include, but are not limited to, simian (e.g., SAV 25), bovine, canine, porcine adenoviruses.

The adenoviral vector is preferably replication-deficient. By "replication-deficient" is meant that the adenoviral vector comprises an adenoviral genome that lacks at least one replication-essential gene function (i.e., such that the adenoviral vector does not replicate in typical host cells, especially those in the human patient that could be infected by the adenoviral vector in the course of treatment in accordance with the invention). A deficiency in a gene, gene function, or gene or genomic region, as used herein, is defined as a deletion of sufficient genetic material of the viral genome to impair or obliterate the function of the gene whose nucleic acid sequence was deleted in whole or in part. While deletion of genetic material is preferred, mutation of genetic material by addition or substitute also is appropriate for disrupting gene function. Replication-essential gene functions are those gene functions that are required for replication (e.g., propagation) and are encoded by, for example, the adenoviral early regions (e.g., the E1, E2, and E4 regions), late regions (e.g., the L1-L5 regions), genes involved in viral packaging (e.g., the IVa2 gene), and virus-associated RNAs (e.g., VA-RNA1 and/or VA-RNA-2). More preferably, the replication-deficient adenoviral vector comprises an adenoviral genome deficient in at least one replication-essential gene function of one or more regions of the adenoviral genome. Preferably, the adenoviral vector is deficient in at least one gene function of the E1 region or the E4 region of the adenoviral genome required for viral replication (denoted an E1-deficient adenoviral vector or an E4-deficient adenoviral vector). In addition to a deficiency in the E1 region, the recombinant adenovirus also can have a mutation in the major late promoter (MLP), as discussed in WO 2000/00628. Most preferably, the adenoviral vector is deficient in at least one replication-essential gene function (desirably all replication-essential gene functions) of the E1 region and at least part of the nonessential E3 region (e.g., an XbaI deletion of the E3 region) (denoted an E1/E3-deficient adenoviral vector). With respect to the E1 region, the adenoviral vector can be deficient in part or all of the E1A region and part or all of the E1B region, e.g., in at least one replication-essential gene function of each of the E1A and E1B regions. When the adenoviral vector is deficient in at least one replication-essential gene function in one region of the adenoviral genome (e.g., an E1- or E1/E3-deficient adenoviral vector), the adenoviral vector is referred to as "singly replication-deficient."

The adenoviral vector of the invention can be "multiply replication-deficient," meaning that the adenoviral vector is deficient in one or more replication-essential gene functions in each of two or more regions of the adenoviral genome. For example, the aforementioned E1-deficient or E1/E3-deficient adenoviral vector can be further deficient in at least one replication-essential gene function of the E4 region (denoted an E1/E4- or E1/E3/E4-deficient adenoviral vector), and/or the E2 region (denoted an E1/E2- or E1/E2/E3-deficient adenoviral vector), preferably the E2A region (denoted an E1/E2A- or E1/E2A/E3-deficient adenoviral vector). Ideally, the adenoviral vector lacks replication-essential gene functions of only those replication-essential gene functions encoded by the early regions of the adenoviral genome, although this is not required in all contexts of the invention. A preferred multiply-deficient adenoviral vector comprises an adenoviral genome having deletions of nucleotides 457-3332 of the E1 region, nucleotides 28593-30470 of the E3 region, nucleotides 32826-35561 of the E4 region, and, optionally, nucleotides 10594-10595 of the region encoding VA-RNA1. However, other deletions may be appropriate. Nucleotides 356-3329 or 356-3510 can be removed to create a deficiency in replication-essential E1 gene functions. Nucleotides 28594-30469 can be deleted from the E3 region of the adenoviral genome. While the specific nucleotide designations recited above correspond to the adenoviral serotype 5 genome, the corresponding nucleotides for non-serotype 5 adenoviral genomes can easily be determined by those of ordinary skill in the art.

The adenoviral vector, when multiply replication-deficient, especially in replication-essential gene functions of the E1 and E4 regions, preferably includes a spacer element to provide viral growth in a complementing cell line similar to that achieved by singly replication-deficient adenoviral vectors, particularly an E1-deficient adenoviral vector. The spacer element can contain any sequence or sequences which are of a desired length, such as sequences at least about 15 base pairs (e.g., between about 15 base pairs and about 12,000 base pairs), preferably about 100 base pairs to about 10,000 base pairs, more preferably about 500 base pairs to about 8,000 base pairs, even more preferably about 1,500 base pairs to about 6,000 base pairs, and most preferably about 2,000 to about 3,000 base pairs in length. The spacer element sequence can be coding or non-coding and native or non-native with respect to the adenoviral genome, but does not restore the replication-essential function to the deficient region. The use of a spacer in an adenoviral vector is described in U.S. Pat. No. 5,851,806. In one embodiment of the inventive method, the replication-deficient or conditionally-replicating adenoviral vector is an E1/E4-deficient adenoviral vector wherein the L5 fiber region is retained, and a spacer is located between the L5 fiber region and the right-side ITR. More preferably, in such an adenoviral vector, the E4 polyadenylation sequence alone or, most preferably, in combination with another sequence, exists between the L5 fiber region and the right-side ITR, so as to sufficiently separate the retained L5 fiber region from the right-side ITR, such that viral production of such a vector approaches that of a singly replication-deficient adenoviral vector, particularly an E1-deficient adenoviral vector.

The adenoviral vector can be deficient in replication-essential gene functions of only the early regions of the adenoviral genome, only the late regions of the adenoviral genome, and both the early and late regions of the adenoviral genome. The adenoviral vector also can have essentially the entire adenoviral genome removed, in which case it is preferred that at least either the viral ITRs and one or more promoters or the viral ITRs and a packaging signal are left intact (i.e., an adenoviral amplicon). The 5' or 3' regions of the adenoviral genome comprising ITRs and packaging sequence need not originate from the same adenoviral serotype as the remainder of the viral genome. For example, the 5' region of an adenoviral serotype 5 genome (i.e., the region of the genome 5' to the adenoviral E1 region) can be replaced with the corresponding region of an adenoviral serotype 2 genome (e.g., the Ad5 genome region 5' to the E1 region of the adenoviral genome is replaced with nucleotides 1-456 of the Ad2 genome). Suitable replication-deficient adenoviral vectors, including multiply replication-deficient adenoviral vectors, are disclosed in U.S. Pat. Nos. 5,837, 511, 5,851,806, 5,994,106, US 2001/0043922, US 2002/

0004040, US 2002/0031831, US 2002/0110545, WO 1995/34671, WO 1997/12986, and WO 1997/21826. Ideally, the replication-deficient adenoviral vector is present in a pharmaceutical composition virtually free of replication-competent adenovirus (RCA) contamination (e.g., the pharmaceutical composition comprises less than about 1% of RCA contamination). Most desirably, the pharmaceutical composition is RCA-free. Adenoviral vector compositions and stocks that are RCA-free are described in U.S. Pat. Nos. 5,944,106, 6,482,616, US 2002/0110545 and WO 1995/34671.

Therefore, in a preferred embodiment, the expression vector of the inventive method is a multiply replication-deficient adenoviral vector lacking all or part of the E1 region, all or part of the E3 region, all or part of the E4 region, and, optionally, all or part of the E2 region. It is believed that multiply deficient vectors are particularly suited for delivery of exogenous nucleic acid sequences to the ear. Adenoviral vectors deficient in at least one replication-essential gene function of the E1 region are most commonly used for gene transfer in vivo. However, currently used singly replication-deficient adenoviral vectors can be detrimental to the sensitive cells of the epithelium of the inner ear, causing damage to the very cells to be treated. Adenoviral vectors that are deficient in at least one replication-essential gene function of the E4 region, particularly adenoviral vectors deficient in replication-essential gene functions of the E4 region and the E1 region, are less toxic to cells than E1-deficient adenoviral vectors (see, for example, Wang, et al. (1996) *Nature Med.* 2(6):714-716 and U.S. Pat. No. 6,228,646). Accordingly, damage to existing hair cells and supporting cells can be minimized by employing an E1,E4-deficient adenoviral vector to deliver the nucleic acid sequence encoding the atonal-associated factor to inner ear cells.

In this regard, it has been observed that an at least E4-deficient adenoviral vector expresses a transgene at high levels for a limited amount of time in vivo and that persistence of expression of a transgene in an at least E4-deficient adenoviral vector can be modulated through the action of a trans-acting factor, such as HSV ICP0, Ad pTP, CMV-IE2, CMV-IE86, HIV tat, HTLV-tax, HBV-X, AAV Rep 78, the cellular factor from the U205 osteosarcoma cell line that functions like HSV ICP0, or the cellular factor in PC12 cells that is induced by nerve growth factor, among others. In view of the above, the multiply deficient adenoviral vector (e.g., the at least E4-deficient adenoviral vector) or a second expression vector comprises a nucleic acid sequence encoding a trans-acting factor that modulates the persistence of expression of the nucleic acid sequence encoding the atonal-associated factor, as described in, for example, U.S. Pat. Nos. 6,225,113, 6,660,521, 6,649,373, and WO 2000/34496.

Replication-deficient adenoviral vectors are typically produced in complementing cell lines that provide gene functions not present in the replication-deficient adenoviral vectors, but required for viral propagation, at appropriate levels in order to generate high titers of viral vector stock. A preferred cell line complements for at least one and preferably all replication-essential gene functions not present in a replication-deficient adenovirus. The complementing cell line can complement for a deficiency in at least one replication-essential gene function encoded by the early regions, late regions, viral packaging regions, virus-associated RNA regions, or combinations thereof, including all adenoviral functions (e.g., to enable propagation of adenoviral amplicons). Most preferably, the complementing cell line complements for a deficiency in at least one replication-essential gene function (e.g., two or more replication-essential gene functions) of the E1 region of the adenoviral genome, particularly a deficiency in a replication-essential gene function of each of the E1A and E1B regions. In addition, the complementing cell line can complement for a deficiency in at least one replication-essential gene function of the E2 (particularly as concerns the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome. The cell line preferably is further characterized in that it contains the complementing genes in a non-overlapping fashion with the adenoviral vector, which minimizes, and practically eliminates, the possibility of the vector genome recombining with the cellular DNA. Accordingly, the presence of replication competent adenoviruses (RCA) is minimized if not avoided in the vector stock, which, therefore, is suitable for certain therapeutic purposes, especially gene therapy purposes. The lack of RCA in the vector stock avoids the replication of the adenoviral vector in non-complementing cells. Construction of such a complementing cell lines involve standard molecular biology and cell culture techniques, such as those described by Sambrook, et al. (1989) *Molecular Cloning, a Laboratory Manual,* 2d edition, Cold Spring Harbor Press, Cold Spring Harbor, N.Y.; and Ausubel, et al. (1994) *Current Protocols in Molecular Biology,* Greene Publishing Associates and John Wiley & Sons, New York, N.Y.

Complementing cell lines for producing the adenoviral vector include, but are not limited to, 293 cells (see, e.g., Graham, et al. (1977) *J. Gen. Virol.* 36:59-72), PER.C6 cells (see, e.g., WO 1997/00326, U.S. Pat. Nos. 5,994,128 and 6,033,908), and 293-ORF6 cells (see, e.g., WO 1995/34671 and Brough, et al. (1997) *J. Virol.* 71:9206-9213). In some instances, the complementing cell will not complement for all required adenoviral gene functions. Helper viruses can be employed to provide the gene functions in trans that are not encoded by the cellular or adenoviral genomes to enable replication of the adenoviral vector. Adenoviral vectors can be constructed, propagated, and/or purified using the materials and methods set forth, for example, in U.S. Pat. Nos. 5,965,358, 5,994,128, 6,033,908, 6,168,941, 6,329,200, 6,383,795, 6,440,728, 6,447,995, 6,475,757, US 2002/0034735, WO 1998/53087, WO 1998/56937, WO 1999/15686, WO 1999/54441, WO 2000/12765, WO 2001/77304, and WO 2002/29388, as well as the other references identified herein. Non-group C adenoviral vectors, including adenoviral serotype 35 vectors, can be produced using the methods set forth in, for example, U.S. Pat. Nos. 5,837,511 5,849,561, WO 1997/12986 and WO 1998/53087. Moreover, numerous adenoviral vectors are available commercially.

The adenoviral vector's coat protein can be modified so as to decrease the adenoviral vector's ability or inability to be recognized by a neutralizing antibody directed against the wild-type coat protein. Such modifications are useful for multiple rounds of administration. Similarly, the coat protein of the adenoviral vector can be manipulated to alter the binding specificity or recognition of the adenoviral vector for a viral receptor on a potential host cell. Such manipulations can include deletion or substitution of regions of the fiber, penton, hexon, pIIIa, pVI, and/or pIX, insertions of various native or non-native ligands into portions of the coat protein, and the like. Manipulation of the coat protein can broaden the range of cells infected by the adenoviral vector or enable targeting of the adenoviral vector to a specific cell type. The ability of an adenoviral vector to recognize a potential host cell can be modulated without genetic manipulation of the coat protein, i.e., through use of a bi-specific molecule. For instance, complexing an adenovirus with a bispecific molecule comprising a penton base- or fiber-binding domain and a domain that selectively binds a particular cell surface binding site enables the targeting of the adenoviral vector to a particular cell type.

Preferably, the adenoviral capsid is modified to display a non-native amino acid sequence. The non-native amino acid sequence can be inserted into or in place of an internal coat protein sequence (e.g., within an exposed loop of an adenoviral fiber protein) or fused to the terminus of an adenoviral coat protein (e.g., fused to the C-terminus of an adenoviral fiber protein, optionally using a linker or spacer sequence). The non-native amino acid sequence can be conjugated to any of the adenoviral coat proteins to form a chimeric coat protein. Therefore, for example, the non-native amino acid sequence of the invention can be conjugated to, inserted into, or attached to a fiber protein, a penton base protein, a hexon protein, proteins IX, VI, or IIIc, etc. The sequences of such proteins, and methods for employing them in recombinant proteins, are well known in the art (see, e.g., U.S. Pat. Nos. 5,543,328, 5,559,099, 5,712,136, 5,731,190, 5,756,086, 5,770,442, 5,846,782, 5,962,311, 5,965,541, 5,846,782, 6,057,155, 6,127,525, 6,153,435, 6,329,190, 6,455,314, 6,465,253, 6,576,456, US 2001/0047081, US 2003/0099619, WO 1996/07734, WO 1996/26281, WO 1997/20051, WO 1998/07877, WO 1998/07865, WO 1998/40509, WO 1998/54346, WO 2000/15823, WO 2001/58940, and WO 2001/92549). The coat protein portion of the chimeric coat protein can be a full-length adenoviral coat protein to which the ligand domain is appended, or it can be truncated, e.g., internally or at the C- and/or N-terminus. The coat protein portion need not, itself, be native to the adenoviral vector.

Where the ligand is attached to the fiber protein, preferably it does not disturb the interaction between viral proteins or fiber monomers. Thus, the non-native amino acid sequence preferably is not itself an oligomerization domain, as such can adversely interact with the trimerization domain of the adenovirus fiber. Preferably the ligand is added to the virion protein, and is incorporated in such a manner as to be readily exposed to the substrate (e.g., at the N- or C-terminus of the protein, attached to a residue facing the substrate, positioned on a peptide spacer to contact the substrate, etc.) to maximally present the non-native amino acid sequence to the substrate. Ideally, the non-native amino acid sequence is incorporated into an adenoviral fiber protein at the C-terminus of the fiber protein (and attached via a spacer) or incorporated into an exposed loop (e.g., the HI loop) of the fiber to create a chimeric coat protein. Where the non-native amino acid sequence is attached to or replaces a portion of the penton base, preferably it is within the hypervariable regions to ensure that it contacts the substrate. Where the non-native amino acid sequence is attached to the hexon, preferably it is within a hypervariable region (Miksza, et al. (1996) *J. Virol.* 70(3):1836-44). Use of a spacer sequence to extend the non-native amino acid sequence away from the surface of the adenoviral particle can be advantageous in that the non-native amino acid sequence can be more available for binding to a receptor and any steric interactions between the non-native amino acid sequence and the adenoviral fiber monomers is reduced.

A chimeric viral coat protein comprising a non-native ligand is desirably able to direct entry into cells of the viral, i.e., adenoviral, vector comprising the coat protein that is more efficient than entry into cells of a vector that is identical except for comprising a wild-type viral coat protein rather than the chimeric viral coat protein. Preferably, the chimeric virus coat protein binds a novel endogenous binding site present on the cell surface that is not recognized, or is poorly recognized by a vector comprising a wild-type coat protein.

In addition, the adenoviral capsid proteins can be altered to reduce or ablate binding to native adenoviral receptors (i.e., receptors bound by wild-type adenovirus). In particular, the portion of the adenoviral fiber protein which interacts with the coxsackie and adenovirus receptor (CAR) can be mutated by deletion, substitution, repositioning within the fiber protein, etc., such that the adenoviral fiber protein does not bind CAR. Likewise, the portion of the adenoviral penton protein that interacts with integrins can be altered to ablate native integrin binding. To reduce native binding and transduction of the replication-deficient or conditionally-replicating adenoviral vector, the native binding sites located on adenoviral coat proteins which mediate cell entry, e.g., the fiber and/or penton base, are absent or disrupted. Two or more of the adenoviral coat proteins are believed to mediate attachment to cell surfaces (e.g., the fiber and penton base). Any suitable technique for altering native binding to a host cell (e.g., a mesothelial cell or hepatocyte) can be employed. For example, exploiting differing fiber lengths to ablate native binding to cells can be accomplished via the addition of a binding sequence to the penton base or fiber knob. This addition can be done either directly or indirectly via a bispecific or multispecific binding sequence. Alternatively, the adenoviral fiber protein can be modified to reduce the number of amino acids in the fiber shaft, thereby creating a "short-shafted" fiber (as described in, for example, U.S. Pat. No. 5,962,311). The fiber proteins of some adenoviral serotypes are naturally shorter than others, and these fiber proteins can be used in place of the native fiber protein to reduce native binding of the adenovirus to its native receptor. For example, the native fiber protein of an adenoviral vector derived from serotype 5 adenovirus can be switched with the fiber protein from adenovirus serotypes 40 or 41.

In this regard, the adenoviral vector can be modified to include an adenoviral coat protein (e.g., fiber, penton, or hexon protein) from a different serotype of adenovirus. For example, an adenoviral serotype 5 adenovirus can be modified to display an adenovirus serotype 35 fiber, which, in turn, can optionally comprise one or more non-native amino acid ligands. It is possible to utilize an adenoviral vector which does not naturally infect cell types of the inner ear to target the vector to a particular cell type. Alternatively, an adenoviral vector which naturally transduces cells of the inner ear can be modified to display an adenoviral fiber protein and/or adenoviral penton base derived from an adenovirus which has no natural tropism for target cells, which adenoviral vector can display a non-native amino acid sequence that enables transduction of target cells.

In another embodiment, the nucleic acid residues associated with native substrate binding can be mutated (see, e.g., WO 2000/15823; Einfeld, et al. (2001) *J. Virol.* 75(23): 11284-11291; van Beusechem, et al. (2002) *J. Virol.* 76(6): 2753-2762) such that the adenoviral vector incorporating the mutated nucleic acid residues is less able to bind its native substrate. For example, adenovirus serotypes 2 and 5 transduce cells via binding of the adenoviral fiber protein to the coxsackievirus and adenovirus receptor (CAR) and binding of penton proteins to integrins located on the cell surface. Accordingly, the replication-deficient or conditionally-replicating adenoviral vector of the inventive method can lack native binding to CAR and/or exhibit reduced native binding to integrins. To reduce native binding of the replication-deficient or conditionally-replicating adenoviral vector to host cells, the native CAR and/or integrin binding sites (e.g., the RGD sequence located in the adenoviral penton base) are removed or disrupted.

Modifications to adenoviral coat proteins can enhance the resulting adenoviral vectors' ability to evade the host immune system. In one embodiment, the adenoviral vector is selectively targeted to scarred epithelial cells (e.g., regions of the epithelium missing endogenous, functional hair cells) by ablation of native binding of the adenoviral vector to CAR and/or integrins and incorporation into the adenoviral capsid one or more non-native ligands. Suitable ligands that mediate transduction via a specific receptor can be determined using routine library display techniques (such as phage display) and include, for example, ligands bound by EGF and ligands from the FGF family of peptides. Other examples of non-native amino acid sequences and their substrates include, but are not limited to, short (e.g., 6 amino acids or less) linear stretches of amino acids recognized by integrins, as well as polyamino acid sequences such as polylysine, polyarginine, etc. Non-native amino acid sequences for generating chimeric adenoviral coat proteins are further described in U.S. Pat. No. 6,455,314 and WO 2001/92549.

Suitable modifications to an adenoviral vector are described in U.S. Pat. Nos. 5,543,328, 5,559,099, 5,712,136, 5,731,190, 5,756,086, 5,770,442, 5,846,782, 5,871,727, 5,885,808, 5,922,315, 5,962,311, 5,965,541, 6,057,155, 6,127,525, 6,153,435, 6,329,190, 6,455,314, 6,465,253, US 2001/0047081, US 2002/0099024, US 2002/0151027, WO 1996/07734, WO 1996/26281, WO 1997/20051, WO 1998/07865, WO 1998/07877, WO 1998/40509, WO 1998/54346, WO 2000/15823, WO 2001/58940, and WO 2001/92549. The construction of adenoviral vectors is well understood in the art. Adenoviral vectors can be constructed and/or purified using the methods set forth, for example, in U.S. Pat. Nos. 5,965,358, 6,168,941, 6,329,200, 6,383,795, 6,440,728, 6,447,995, 6,475,757, WO 1998/53087, WO 1998/56937, WO 1999/15686, WO 1999/54441, WO 2000/12765, WO 2001/77304, and WO 2002/29388, as well as the other references identified herein. Moreover, numerous expression vectors, including adenoviral vectors, are available commercially. Adeno-associated viral vectors can be constructed and/or purified using the methods set forth, for example, in U.S. Pat. No. 4,797,368 and Laughlin, et al. (1983) *Gene* 23:65-73.

The selection of an expression vector for use in the inventive method depends on a variety of factors such as, for example, the host, immunogenicity of the vector, the desired duration of protein production, the target cell, and the like. As each type of expression vector has distinct properties, the inventive method can be tailored to any particular situation. Moreover, more than one type of expression vector can be used to deliver the nucleic acid sequence to the target cell. Thus, the invention provides a method of improving the sensory perception of an animal, wherein the method comprises administering to the inner ear at least two different expression vectors, each comprising a nucleic acid sequence encoding an atonal-associated factor and/or a nucleic acid sequence encoding a co-transcription factor and/or inhibitor of a gene silencing complex. Preferably, the target cell in the inner ear, e.g., a supporting cell, is contacted with an adenoviral vector and an HSV vector, in that adenoviral vectors efficiently transduce supporting cells and HSV vectors efficiently transduce neurons. One of ordinary skill in the art will appreciate the ability to capitalize on the advantageous properties of multiple delivery systems to treat or study sensory disorders of the inner ear.

Nucleic Acid Molecules.

The expression vector of this invention harbors nucleic acid molecules, the expression of which facilitates the regeneration of hair cells and hearing restoration. Ideally, the nucleic acid molecules encode an atonal-associated factor and can further encode a co-transcription factor and/or inhibitor of a gene silencing complex. One of ordinary skill in the art will appreciate that any transcription factor, e.g., Math1 or Hath1 or co-transcription factor, can be modified or truncated and retain transcription activating activity. As such, therapeutic fragments (i.e., those fragments having biological activity sufficient to, for example, activate transcription) also are suitable for incorporation into the expression vector. Likewise, a fusion protein composed of a transcription factor or a therapeutic fragment thereof and, for example, a moiety that stabilizes peptide conformation, also can be present in the expression vector.

Nucleic acid molecules (i.e., encoding an atonal-associated factor and/or a co-transcription factor and/or inhibitor of a gene silencing complex) are desirably present as part of an expression cassette, i.e., a particular base sequence that possesses functions which facilitate subcloning and recovery of a nucleic acid molecule (e.g., one or more restriction sites) or expression of a nucleic acid molecule (e.g., polyadenylation or splice sites). When the expression cassette is an adenoviral vector, the nucleic acid molecule of interest (e.g., encoding an atonal-associated factor and/or a co-transcription factor and/or inhibitor of a gene silencing complex) can be located in the E1 region (e.g., replaces the E1 region in whole or in part) or can be located in the E4 region of the adenoviral genome. When positioned in the E4 region, a spacer sequence is not required. The expression cassette is preferably inserted in a 3'→5' orientation, e.g., oriented such that the direction of transcription of the expression cassette is opposite that of the surrounding adenoviral genome. While a single expression cassette can be inserted into an adenoviral vector for expressing an atonal-associated factor and/or a co-transcription factor and/or inhibitor of a gene silencing complex, in other embodiments, the adenoviral vector can include multiple expression cassettes harboring nucleic acid molecules encoding the encoding atonal-associated factor and/or a co-transcription factor and/or inhibitor of a gene silencing complex, wherein said cassettes can replace any of the deleted regions of the adenoviral genome. The insertion of an expression cassette into the adenoviral genome (e.g., the E1 region of the genome) can be facilitated by known methods, for example, by the introduction of a unique restriction site at a given position of the adenoviral genome. As set forth above, preferably the E3 region of the adenoviral vector is deleted, and the E4 region is replaced by a spacer element.

For expression, the nucleic acid molecule of interest is operably linked to regulatory sequences necessary for said expression, e.g., a promoter. A "promoter" is a DNA sequence that directs the binding of RNA polymerase and thereby promotes RNA synthesis. A nucleic acid molecule is "operably linked" to a promoter when the promoter is capable of directing transcription of that nucleic acid molecule. A promoter can be native or non-native to the nucleic acid molecule to which it is operably linked. Any promoter (i.e., whether isolated from nature or produced by recombinant DNA or synthetic techniques) can be used in connection with the invention to provide for transcription of the nucleic acid molecule. The promoter preferably is capable of directing transcription in a eukaryotic (desirably mammalian) cell. The functioning of the promoter can be altered by the presence of one or more enhancers (e.g., the CMV immediate early enhancer) and/or silencers.

The invention preferentially employs a viral promoter. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, Rous sarcoma virus (RSV) promoters, such as the RSV long terminal repeat, mouse mammary tumor virus (MMTV) promoters, HSV promoters, such as the Lap2 promoter or the herpes thymidine kinase promoter (Wagner, et al. (1981) *Proc. Natl. Acad. Sci. USA* 78:144-145), promoters derived from SV40 or Epstein Barr virus, an adeno-associated viral promoter, such as the p5 promoter, and the like. Preferably, the viral promoter is an adenoviral promoter, such as the Ad2 or Ad5 major late promoter and tripartite leader, a CMV promoter (murine or human in origin), or an RSV promoter.

The promoter need not be a viral promoter. For example, the promoter can be a cellular promoter, i.e., a promoter that drives expression of a cellular protein. Preferred cellular promoters for use in the invention will depend on the desired expression profile to produce the therapeutic agent(s). In one aspect, the cellular promoter is preferably a constitutive promoter that works in a variety of cell types. Suitable constitutive promoters can drive expression of genes encoding transcription factors, housekeeping genes, or structural genes common to eukaryotic cells. For example, the Ying Yang 1 (YY1) transcription factor (also referred to as NMP-1, NF-E1, and UCRBP) is a ubiquitous nuclear transcription factor that is an intrinsic component of the nuclear matrix (Guo, et al. (1995) *Proc. Natl. Acad. Sci. USA* 92:10526-10530). JEM-1 (also known as HGMW and BLZF-1; Tong, et al. (1998) *Leukemia* 12(11):1733-1740; Tong, et al. (2000) *Genomics* 69(3):380-390), a ubiquitin promoter, specifically UbC (Marinovic, et al. (2002) *J. Biol. Chem.* 277(19):16673-16681), a (3-actin promoter, such as that derived from chicken, and the like are appropriate for use in the inventive method.

Many of the above-described promoters are constitutive promoters. Instead of being a constitutive promoter, the promoter can be an inducible promoter, i.e., a promoter that is up- and/or down-regulated in response to appropriate signals. For instance, suitable inducible promoter systems include, but are not limited to, the IL-8 promoter, the metallothionine inducible promoter system, the bacterial lacZYA expression system, the tetracycline expression system, and the T7 polymerase system. Further, promoters that are selectively activated at different developmental stages (e.g., globin genes are differentially transcribed from globin-associated promoters in embryos and adults) can be employed. The promoter sequence that regulates expression of the nucleic acid molecule can contain at least one heterologous regulatory sequence responsive to regulation by an exogenous agent. The regulatory sequences are preferably responsive to exogenous agents such as, but not limited to, drugs, hormones, or other gene products. For example, the regulatory sequences, e.g., promoter, preferably are responsive to glucocorticoid receptor-hormone complexes, which, in turn, enhance the level of transcription of a therapeutic peptide or a therapeutic fragment thereof.

Preferably, the promoter is a tissue-specific promoter, i.e., a promoter that is preferentially activated in a given tissue and results in expression of a gene product in the tissue where activated. A tissue specific promoter for use in this invention can be chosen by the ordinarily skilled artisan based upon the target tissue or cell-type. Suitable promoters include, but are not limited to, BRN.3C, BRN 3.1, the POU ORF3 factor promoter, BRK1, BRK3, the chordin promoter, the noggin promoter, the jagged1 promoter, the jagged2 promoter, and the notch1 promoter. Preferred tissue-specific promoters for use in this invention are specific to supporting cells or sensory hair cells, such as an atonal promoter or a myosin VIIa promoter, which function in hair cells, or a hes-1 promoter, which functions in supporting cells. Ideally, a promoter is selected that promotes transgene expression in scarred epithelium.

A promoter also can be selected for use in this invention by matching its particular pattern of activity with the desired pattern and level of expression of the desired protein (e.g., the atonal-associated factor). Alternatively, a hybrid promoter can be constructed which combines the desirable aspects of multiple promoters. For example, a CMV-RSV hybrid promoter combining the CMV promoter's initial rush of activity with the RSV promoter's high maintenance level of activity is especially preferred for use in many embodiments of the inventive method. It is also possible to select a promoter with an expression profile that can be manipulated by an investigator.

Along these lines, to optimize protein production, preferably the nucleic acid molecule further includes a polyadenylation site following the coding region of the nucleic acid molecule. Any suitable polyadenylation sequence can be used, including a synthetic optimized sequence, as well as the polyadenylation sequence of BGH (Bovine Growth Hormone), polyoma virus, TK (Thymidine Kinase), EBV (Epstein Barr Virus), and the papillomaviruses, including human papillomaviruses and BPV (Bovine Papilloma Virus). A preferred polyadenylation sequence is the SV40 (Human Sarcoma Virus-40) polyadenylation sequence. Also, preferably all the proper transcription signals (and translation signals, where appropriate) are correctly arranged such that the nucleic acid molecule is properly expressed in the cells into which it is introduced. If desired, the nucleic acid molecule also can incorporate splice sites (i.e., splice acceptor and splice donor sites) to facilitate mRNA production. Moreover, if the nucleic acid molecule encodes a protein or peptide, which is a processed or secreted protein or acts intracellularly, preferably the nucleic acid molecule further includes the appropriate sequences for processing, secretion, intracellular localization, and the like.

In certain embodiments, it may be advantageous to modulate expression of the atonal-associated factor and/or a co-transcription factor and/or inhibitor of a gene silencing complex. An especially, preferred method of modulating expression of a nucleic acid molecule involves the addition of site-specific recombination sites on the expression vector. Contacting an expression vector having site-specific recombination sites with a recombinase will either up- or down-regulate transcription of a coding sequence, or simultaneously up-regulate transcription of one coding sequence and down-regulate transcription of another, through the recombination event. Use of site-specific recombination to modulate transcription of a nucleic acid sequence is described in, for example, U.S. Pat. Nos. 5,801,030, 6,063,627 and WO 97/09439.

Several options are available for delivering nucleic acid molecules encoding the atonal-associated factor and/or a co-transcription factor and/or inhibitor of a gene silencing complex to the inner ear. The nucleic acid molecule encoding the atonal-associated factor can also encode a co-transcription factor and/or inhibitor of a gene silencing complex. The expression vector alternatively, or in addition, can include multiple expression cassettes encoding atonal-associated factor and/or a co-transcription factor and/or inhibitor of a gene silencing complex. The multiple coding sequences can be operably linked to different promoters, e.g., different promoters having dissimilar levels and patterns of activity. Alternatively, the multiple coding sequences can be operably linked to the same promoter to form a polycistronic element. The invention also contemplates administering to the inner ear a cocktail of expression vectors, wherein each expression vectors encode an atonal-associated factor and/or a co-transcription factor and/or inhibitor of a gene silencing complex. The cocktail of expression vectors can further include different types of expression vectors, e.g., adenoviral vectors and adeno-associated viral vectors.

In view of the above, the invention further provides an adenoviral vector harboring a nucleic acid molecule(s) encoding an atonal-associated factor (e.g., Math1 or Hath1) and/or a co-transcription factor and/or inhibitor of a gene silencing complex, wherein the nucleic acid molecule(s) is operably linked to regulatory sequences necessary for expression of the atonal-associated factor and/or a co-transcription factor and/or inhibitor of a gene silencing complex. The adenoviral vector is deficient in at least one replication-essential gene function of at least the E4 region. The nucleic acid molecule can be obtained from any source, e.g., isolated from nature, synthetically generated, isolated from a genetically engineered organism, and the like. Appropriate adenoviral vectors and regulatory sequences are discussed herein.

Moreover, the invention further provides a method of generating a hair cell in differentiated sensory epithelia in vivo. The method involves contacting differentiated sensory epithelial cells with an adenoviral vector (a) deficient in one or more replication-essential gene functions of the E1 region, the E4 region, and, optionally, one or more gene functions the E3 region, (b) having a spacer in the E4 region, and (c) harboring a nucleic acid molecule(s) encoding an atonal-associated factor and/or a co-transcription factor and/or inhibitor of a gene silencing complex. The nucleic acid molecule(s) is expressed to produce the atonal-associated factor and/or a co-transcription factor and/or inhibitor of a gene silencing complex such that a hair cell is generated. While the adenoviral vector can be used to generate hair cells in vivo (and therefore is useful for prophylactically or therapeutically treat a hearing disorder or a balance disorder), transdifferentiation of supporting cells can occur in vitro and, thus, can be used in methods of research.

Routes of Administration.

One skilled in the art will appreciate that suitable methods of administering an expression vector, such as an adenoviral vector, to the inner ear are available. Although more than one route can be used to administer a particular expression vector, a particular route can provide a more immediate and more effective reaction than another route. Accordingly, the described routes of administration are merely exemplary and are in no way limiting.

No matter the route of administration, an expression vector of the inventive method ideally reaches the sensory epithelium of the inner ear. The most direct routes of administration, therefore, entail surgical procedures which allow access to the interior of the structures of the inner ear. Inoculation via cochleostomy allows administration of an expression vector directly to the regions of the inner ear associated with hearing. Cochleostomy involves drilling a hole through the cochlear wall, e.g., in the otic capsule below the stapedial artery as described in Kawamoto, et al. ((2001) *Molecular Therapy* 4(6):575-585), and release of a pharmaceutical composition containing the expression vector. Administration to the endolymphatic compartment is particularly useful for administering an adenoviral vector to the areas of the inner ear responsible for hearing. Alternatively, an expression vector can be administered to the semicircular canals via canalostomy. Canalostomy provides for transgene expression in the vestibular system and the cochlea, whereas cochleostomy does not provide as efficient transduction in the vestibular space. The risk of damage to cochlear function is reduced using canalostomy in as much as direct injection into the cochlear space can result in mechanical damage to hair cells (Kawamoto, et al., supra). Administration procedures also can be performed under fluid (e.g., artificial perilymph), which can include factors to alleviate side effects of treatment or the administration procedure, such as apoptosis inhibitors or anti-inflammatories.

Another direct route of administration to the inner ear is through the round window, either by injection or topical application to the round window. Administration via the round window is especially preferred for delivering an adenoviral vector to the perilymphatic space. Transgene expression in cochlear and vestibular neurons and cochlear sensory epithelia has been observed following administration of expression vectors via the round window (Staecker, et al. (2001) *Acta Otolaryngol.* 121:157-163). Of note, it appears possible that uptake of expression vectors, in particular non-targeted adenoviral vectors, into cells of the inner ear is not receptor-mediated. In other words, it does not appear that adenoviral infection of cells of the inner ear is mediated by CAR or integrins. To increase transduction of cells in the Organ of Corti following administration to the perilymphatic compartment, an adenoviral vector can display one or more ligands that enhance uptake of the adenoviral vector into target cells (e.g., supporting cells, cells of the stria vascularis, etc.). In this regard, the adenoviral vector can encode one or more adenoviral coat proteins which are modified to reduce native binding (e.g., CAR- and/or integrin-binding) and harbor a non-native amino acid sequence which enhances uptake of the adenoviral vector by target cells of the inner ear.

An expression vector (e.g., adenoviral vector) can be present in a pharmaceutical composition for administration to the inner ear. In certain cases, it may be appropriate to administer multiple applications and/or employ multiple routes, e.g., canalostomy and cochleostomy, to ensure sufficient exposure of supporting cells to the expression vector.

An expression vector can be present in or on a device that allows controlled or sustained release of the expression vector, such as a sponge, meshwork, mechanical reservoir or pump, or mechanical implant. For example, a biocompatible sponge or gelform soaked in a pharmaceutical composition containing the expression vector encoding an atonal-associated factor and/or a co-transcription factor and/or inhibitor of a gene silencing complex is placed adjacent to the round window, through which the expression vector permeates to reach the cochlea (as described in Jero, et al., supra). Mini-osmotic pumps provide sustained release of an expression vector over extended periods of time (e.g., five to seven days), allowing small volumes of composition containing the expression vector to be administered, which can prevent mechanical damage to endogenous sensory cells. The expression vector also can be administered in the form of sustained-release formulations (see, e.g., U.S. Pat. No.

5,378,475) containing, for example, gelatin, chondroitin sulfate, a polyphosphoester, such as bis-2-hydroxyethyl-terephthalate (BHET), or a polylactic-glycolic acid.

Alternatively, the expression vector can be administered parenterally, intramuscularly, intravenously, or intraperitoneally. Preferably, any expression vector parenterally administered to a patient for generating sensory hair cells in the ear is specifically targeted to sensory epithelial cells, such as supporting cells. Desirably, the expression vector is targeted to scarred sensory epithelium to promote generation of exogenous hair cells to replace damaged endogenous hair cells. As discussed herein, an expression vector can be modified to alter the binding specificity or recognition of an expression vector for a receptor on a potential host cell. With respect to adenovirus, such manipulations can include deletion of regions of the fiber, penton, or hexon, insertions of various native or non-native ligands into portions of the coat protein, and the like. One of ordinary skill in the art will appreciate that parenteral administration can require large doses or multiple administrations to effectively deliver the expression vector to the appropriate host cells. Pharmaceutically acceptable carriers for compositions are well-known to those of ordinary skill in the art (see *Pharmaceutics and Pharmacy Practice*, (1982) J.B. Lippincott Co., Philadelphia, Pa., Banker and Chalmers, eds., pages 238-250; *ASHP Handbook on Injectable Drugs* (1986) Toissel, 4$^{th}$ ed., pages 622-630). Although less preferred, the expression vector can also be administered in vivo by particle bombardment, i.e., a gene gun.

One of ordinary skill in the art also will appreciate that dosage and routes of administration can be selected to minimize loss of expression vector due to a host's immune system. For example, for contacting target cells in vivo, it can be advantageous to administer to a host a null expression vector (i.e., an expression vector not harboring the nucleic acid molecule(s) of interest) prior to performing the inventive method. Prior administration of null expression vectors can serve to create an immunity in the host to the expression vector hinder the body's innate clearance mechanisms, thereby decreasing the amount of vector cleared by the immune system.

Dosage.

The dose of expression vector administered to an animal, particularly a human, in accordance with the invention should be sufficient to affect the desired response in the animal over a reasonable time frame. One skilled in the art will recognize that dosage will depend upon a variety of factors, including the age, species, location of damaged sensory epithelia, the pathology in question (if any), and condition or disease state. Dosage also depends on the atonal-associated factor and/or a co-transcription factor and/or inhibitor of a gene silencing complex, as well as the amount of sensory epithelium to be transduced. The size of the dose also will be determined by the route, timing, and frequency of administration as well as the existence, nature, and extent of any adverse side effects that might accompany the administration of a particular expression vector (e.g., surgical trauma) and the desired physiological effect. It will be appreciated by one of ordinary skill in the art that various conditions or disease states, in particular, chronic conditions or disease states, may require prolonged treatment involving multiple administrations.

Suitable doses and dosage regimens can be determined by conventional range-finding techniques known to those of ordinary skill in the art. When the expression vector is a viral vector, most preferably an adenoviral vector, about $10^5$ viral particles to about $10^{12}$ viral particles are delivered to the patient. In other words, a pharmaceutical composition can be administered that includes an expression vector concentration of about $10^5$ particles/ml to about $10^{13}$ particles/ml (including all integers within the range of about $10^5$ particles/ml to about $10^{13}$ particles/ml), preferably about $10^{10}$ particles/ml to about $10^{12}$ particles/ml, and will typically involve the administration of about 0.1 µl to about 100 µl of such a pharmaceutical composition directly to the inner ear. In view of the above, the dose of one administration preferably is at least about $1\times10^6$ particles (e.g., about $4\times10^6$-$4\times10^{12}$ particles), more preferably at least about $1\times10^7$ particles, more preferably at least about $1\times10^8$ particles (e.g., about $4\times10^8$-$4\times10^{11}$ particles), and most preferably at least about $1\times10^9$ particles to at least about $1\times10^{10}$ particles (e.g., about $4\times10^9$-$4\times10^{10}$ particles) of an adenoviral vector harboring a nucleic acid molecule encoding an atonal-associated factor and/or a co-transcription factor and/or inhibitor of a gene silencing complex. Alternatively, the dose of the pharmaceutical composition includes no more than about $1\times10^{14}$ particles, preferably no more than about $1\times10^{13}$ particles, even more preferably no more than about $1\times10^{12}$ particles, even more preferably no more than about $1\times10^{11}$ particles, and most preferably no more than about $1\times10^{10}$ particles (e.g., no more than about $1\times10^9$ particles). In other words, a single dose of pharmaceutical composition can be about $1\times10^6$ particle units (pu), $4\times10^6$ pu, $1\times10^7$ pu, $4\times10^7$ pu, $1\times10^8$ pu, $4\times10^8$ pu, $1\times10^9$ pu, $4\times10^9$ pu, $1\times10^{10}$ pu, $4\times10^{10}$ pu, $1\times10^{11}$ pu, $4\times10^{11}$ pu, $1\times10^{11}$ pu, $4\times10^{11}$ pu, $1\times10^{12}$ pu, or $4\times10^{12}$ pu of the adenoviral vector (e.g., the replication-deficient adenoviral vector). When the expression vector is a plasmid, preferably about 0.5, ng to about 1000 µg of DNA is administered. More preferably, about 0.1 µg to about 500 µg is administered, even more preferably about 1 µg to about 100 µg of DNA is administered. Most preferably, about 50 µg of DNA is administered to the inner ear. Of course, other routes of administration may require smaller or larger doses to achieve a therapeutic effect. Any necessary variations in dosages and routes of administration can be determined by the ordinarily skilled artisan using routine techniques known in the art.

The interior space of the structures of the inner ear is limited. The volume of pharmaceutical composition administered directly into the inner ear structures should be carefully monitored, as forcing too much composition will damage the sensory epithelium. For a human patient, the volume administered is preferably about 10 µl to about 2 ml (e.g., from about 25 µl to about 1.5 ml) of composition. For example, from about 50 µl to about 1 ml (e.g., about 100 µl, 200 µl, 300 µl, 400 µl, 500 µl, 600 µl, 700 µl, 800 µl or 900 µl) of composition can be administered. In one embodiment, the entire fluid contents of the inner ear structure, e.g., the cochlea or semicircular canals, is replaced with pharmaceutical composition. In another embodiment, a pharmaceutical composition including the expression vector of the invention is slowly released into the inner ear structure, such that mechanical trauma is minimized.

It can be advantageous to administer two or more (i.e., multiple) doses of the expression vector harboring a nucleic acid molecule encoding an atonal-associated factor and/or a co-transcription factor and/or inhibitor of a gene silencing complex. The inventive method provides for administration of multiple doses of the nucleic acid molecule encoding an atonal-associated factor and/or a co-transcription factor and/or inhibitor of a gene silencing complex to generate hair cells in the sensory epithelium to change the sensory perception of an animal. For example, at least two doses of an expression vector can be administered to the same ear.

Preferably, the multiple doses are administered while retaining gene expression above background levels. Also preferably, the sensory epithelium of the inner ear is contacted with two doses or more of the expression vector within about 30 days. More preferably, two or more applications are administered to the inner ear within about 90 days. However, three, four, five, six, or more doses can be administered in any time frame (e.g., 2, 7, 10, 14, 21, 28, 35, 42, 49, 56, 63, 70, 77, 85 or more days between doses) so long as gene expression occurs.

Pharmaceutical Composition.

The expression vector of the invention desirably is administered in a pharmaceutical composition, which includes a pharmaceutically acceptable carrier and the expression vector(s). Any suitable pharmaceutically acceptable carrier can be used within the context of the invention, and such carriers are well known in the art. The choice of carrier will be determined, in part, by the particular site to which the composition is to be administered and the particular method used to administer the composition. Ideally, in the context of adenoviral vectors, the pharmaceutical composition preferably is free of replication-competent adenovirus.

Suitable formulations include aqueous and non-aqueous solutions, isotonic sterile solutions, which can contain anti-oxidants, buffers, bacteriostats, and solutes that render the formulation isotonic with the blood or fluid of the inner ear of the intended recipient, and aqueous and non-aqueous sterile suspensions that can include suspending agents, solubilizers, thickening agents, stabilizers, and preservatives. The formulation can include artificial endolymph or perilymph, which are commercially available. The formulations can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets of the kind previously described. Preferably, the pharmaceutically acceptable carrier is a buffered saline solution. More preferably, the expression vector for use in the inventive method is administered in a pharmaceutical composition formulated to protect the expression vector from damage prior to administration. For example, the pharmaceutical composition can be formulated to reduce loss of the expression vector on devices used to prepare, store, or administer the expression vector, such as glassware, syringes, or needles. The pharmaceutical composition can be formulated to decrease the light sensitivity and/or temperature sensitivity of the expression vector. To this end, the pharmaceutical composition preferably includes a pharmaceutically acceptable carrier, such as, for example nanoparticles as well as those carriers described above, and a stabilizing agent selected from the group consisting of polysorbate 80, L-arginine, polyvinylpyrrolidone, trehalose, and combinations thereof. In addition, there are many hydrogel forms that have been extensively used for inner ear drug delivery including, but not limited to, Hydrogel 407 (Otonomy, Inc., San Diego, Calif.) and the like. Use of such a pharmaceutical composition will extend the shelf-life of the vector, facilitate administration, and increase the efficiency of the inventive method. In this regard, a pharmaceutical composition also can be formulated to enhance transduction efficiency. In addition, one of ordinary skill in the art will appreciate that the expression vector, e.g., viral vector, can be present in a composition with other therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the viral vector. Immune system suppressors can be administered in combination with the inventive method to reduce any immune response to the vector itself or associated with a disorder of the inner ear. Angiogenic factors, neurotrophic factors, proliferating agents, and the like can be present in the pharmaceutical composition. Similarly, vitamins and minerals, anti-oxidants, and micronutrients can be co-administered. Antibiotics, i.e., microbicides and fungicides, can be present to reduce the risk of infection associated with gene transfer procedures and other disorders.

Other Considerations.

The inventive method includes administering to the inner ear an expression vector(s) harboring a nucleic acid molecule(s) encoding an atonal-associated factor and/or a co-transcription factor and/or inhibitor of a gene silencing complex to change the sensory perception of an animal by generating hair cells in the sensory epithelium of the inner ear. The nucleic acid molecule encoding the atonal-associated factor can encode multiple (i.e., two, three, or more) atonal-associated factors and/or a co-transcription factor and/or inhibitor of a gene silencing complex, or multiple copies of the same. However, the mere generation of a hair cell does not ensure a change in sensory perception in an animal. A sufficient number of hair cells should be generated, and those sensory hair cells should be linked to a neural network capable of transmitting signals to the brain. Accordingly, while not required, it may be advantageous to provide additional factors to ensure proper reception and transmission of signals to the brain.

As discussed herein, several options are available for delivering multiple coding sequences to the inner ear. The nucleic acid molecule(s) encoding the atonal-associated factor and/or a co-transcription factor and/or inhibitor of a gene silencing complex can encode additional gene products. The expression vector alternatively, or in addition, can include multiple expression cassettes encoding different gene products. Multiple coding sequences can be operably linked to different promoters, e.g., different promoters having dissimilar levels and patterns of activity. Alternatively, the multiple coding sequences can be operably linked to the same promoter to form a polycistronic element. The invention also contemplates administering to the inner ear a cocktail of expression vectors, wherein each expression vector encodes an atonal-associated factor or another gene product beneficial to sensory perception. The cocktail of expression vectors can further comprise different types of expression vectors, e.g., adenoviral vectors and adeno-associated viral vectors.

In one preferred embodiment, the inventive method also contemplates delivery of a nucleic acid molecule encoding at least one neurotrophic agent. Ideally, the neurotrophic agent is a neural growth stimulator, which induces growth, development, and/or maturation of neural processes. Neurotrophic factors also can be administered to protect or maintain existing and developing neurons. For a newly generated hair cell to function properly, a neural network should be in place to transmit neural impulses to the brain. Accordingly, it is advantageous to protect existing neurons associated with the sensory epithelium of the inner ear while generating new hair cells, induce the growth and maturation of new neural processes, and/or simply direct existing neural processes to sensory hair cells. Neurotrophic factors are divided into three subclasses: neuropoietic cytokines; neurotrophins; and the fibroblast growth factors. Ciliary neurotrophic factor (CNTF) is exemplary of neuropoietic cytokines. CNTF promotes the survival of ciliary ganglionic neurons and supports certain neurons that are NGF-responsive. Neurotrophins include, for example, brain-derived neurotrophic factor (BDNF) and nerve growth factor (NGF), which stimulates neurite outgrowth. Other neurotrophic factors include, for example, transforming growth factors, glial cell-line derived neurotrophic factor (GDNF), neurotrophin 3, neurotrophin 4/5, and interleukin 1-β. Neuronotrophic factors enhance neuronal survival and also are suitable for use in the inventive method. It has been postulated that neuronotrophic factors can actually reverse degradation of neurons. Such factors, conceivably, are useful in treating the degeneration of neurons associated with age, infection, or trauma. A preferred neuronotrophic factor is pigment epithelium derived factor (PEDF). PEDF is further described in Chader (1987) *Cell Different.* 20:209-216; Pignolo, et al. (1998) *J. Biol. Chem.* 268(12):8949-8957; U.S. Pat. No. 5,840,686, WO 1993/24529, WO 1999/04806, and WO 2001/58494.

Proliferating agents induce cellular proliferation, preferably proliferation of supporting cells in the inner ear. Multiplying the number of hair cell progenitors maximizes the biological effect of the atonal-associated factor and/or a co-transcription factor and/or inhibitor of a gene silencing complex. Supporting cell proliferation is induced by mitogenic growth factors, such as fibroblast growth factors (FGF, in particular FGF-2), vascular endothelial growth factors (VEGF), epidermal growth factor (EGF), E2F, cell cycle up-regulators, and the like. A nucleic acid sequence encoding a proliferating agent can be administered in conjunction with the nucleic acid molecule(s) encoding an atonal-associated factor and/or a co-transcription factor and/or inhibitor of a gene silencing complex in the inventive method. If desired, the nucleic acid molecule encoding a proliferating agent can be engineered to exert its biological effect only on the cell type to be replicated. For supporting cells, the nucleic acid can include a regulatory sequence that is preferentially activated in supporting cells, e.g., a promoter that is active only in the presence of hes transcription factors. The resulting proliferating agent also can be engineered to prevent secretion into the cellular milieu. Alternatively, a substance can be administered to the inner ear to promote cell proliferation or enhance uptake of the expression vector.

The method of the invention can be part of a treatment regimen involving other therapeutic modalities. It is appropriate, therefore, if the inventive method is employed to prophylactically or therapeutically treat a sensory disorder, namely a hearing disorder or a balance disorder, that has been treated, is being treated, or will be treated with any of a number of other therapies, such as drug therapy or surgery. The inventive method also can be performed in conjunction with the implantation of hearing devices, such as cochlear implants. The inventive method also is particularly suited for procedures involving stem cells to regenerate populations of cells within the inner ear. In this respect, the inventive method can be practiced ex vivo to transduce stem cells, which are then implanted within the inner ear.

The expression vector is preferably administered as soon as possible after it has been determined that an animal, such as a mammal, specifically a human, is at risk for degeneration of sensory hair cells (prophylactic treatment) or has demonstrated reduced numbers or damage of sensory hair cells (therapeutic treatment). Treatment will depend, in part, upon the particular nucleic acid molecule used, the particular atonal-associated factor and/or a co-transcription factor and/or inhibitor of a gene silencing complex expressed, the expression vector, the route of administration, and the cause and extent, if any, of hair cell loss or damage realized.

An expression vector(s) harboring a nucleic acid molecule(s) encoding an atonal-associated factor and/or a co-transcription factor and/or inhibitor of a gene silencing complex can be introduced ex vivo into cells previously removed from a given animal, in particular a human. Such transduced autologous or homologous host cells can be progenitor cells that are reintroduced into the inner ear of the animal or human to express the atonal-associated factor and/or a co-transcription factor and/or inhibitor of a gene silencing complex and differentiate into mature hair cells in vivo. One of ordinary skill in the art will understand that such cells need not be isolated from the patient, but can instead be isolated from another individual and implanted into the patient.

The inventive method also can involve the co-administration of other pharmaceutically active compounds. By "co-administration" is meant administration before, concurrently with, e.g., in combination with the expression vector in the same formulation or in separate formulations, or after administration of the expression vector as described above. For example, factors that control inflammation, such as ibuprofen or steroids, can be co-administered to reduce swelling and inflammation associated with administration of the expression vector. Immunosuppressive agents can be co-administered to reduce inappropriate immune responses related to an inner ear disorder or the practice of the inventive method. Similarly, vitamins and minerals, antioxidants, and micronutrients can be co-administered. Antibiotics, i.e., microbicides and fungicides, can be co-administered to reduce the risk of infection associated with surgical procedures.

The following non-limiting examples are provided to further illustrate the present invention.

Example 1: Synergistic Effects of Isl1 in Atoh1-Mediated Cochlear Hair Cell (HC) Conversion This example provides a detailed RNA-seq analysis of converted hair cells (cHCs) followed by validation with single-cell multiplex qPCR analysis and immunostaining. This analysis identified cHCs in multiple intermediate states of the conversion process that most closely resembled neonatal differentiating HCs, but differed from the progenitors, suggesting a conversion path different from that in normal development. Further, 52 transcription factors were identified that were differentially expressed in cHCs, supporting cells (SCs), and mature HC. Notably, of these transcription factors, overexpression of Isl1 was found to synergistically enhance the efficiency of Atoh1-mediated HC conversion in cochlear explants.

Animals.

The Animal Care and Use Committees of St. Jude Children's Research Hospital approved all protocols performed in this study, and all methods were carried out in accordance with the approved guidelines. Mice were housed in a facility with a 12-hour light/dark cycle and free access to food and water. Fgfr3$^{icreER}$, Atoh1-HA, AChR-EGFP, Ai14 and prestin-YFP mice were obtained as described previously (Liu, et al. (2012) *J. Neurosci.* 32(19):6600-10; Cox, et al. (2012) *J. Assoc. Res. Otolaryngol.* 13(3):295-322; Yamashita, et al. (2015) *PLoS Genetics* 11(9):e1005500; Zuo, et al. (1999) *Proc. Natl. Acad. Sci. USA* 96(24):14100-5). Ai14 mice (referred to herein as tdTomato mice) have a loxP-flanked stop cassette followed by a CAG promoter-driven red fluorescent protein variant (tdTomato) in the Rosa26 locus. The Pval-Cre mice were purchased from The Jackson Laboratory. To label cHCs in vivo, tamoxifen was intraperitonealy injected into Fgfr3$^{icreER+}$; Atoh1-HA$^+$; α9 AChR-EGFP$^+$; tdTomato$^+$ mice at 3 mg/40 g at P12 and 13 as previously described before (Liu, et al. (2012) *J. Neurosci.* 32(19): 6600-10). Fgfr3$^{icreER+}$; tdTomato$^+$ mice were used in the isolation of SCs. During isolation of SCs, cHCs, and OHCs from Pval-Cre$^+$; tdTomato$^+$ mice at P74, strong tdTomato signals were observed in inner hair cells (IHCs), but weak in outer hair cells (OHCs). Therefore, Pval-Cre$^+$; tdTomato$^+$ were used for isolating IHCs.

Transgenic Mouse Lines of Isl1 Ectopic Expression.

The coding region of murine Isl1 gene was cloned by RT-PCR using mouse cochlear total RNA as template. The Isl1 gene was inserted right before the IRES sequence of the pCAGGS-S-stop-IRES-mCherry vector (Walters, et al. (2017) *Cell Reports* 19:307-320). The 8.0 kb DNA fragment of CAG-flox-stop-flox-Isl1-IRES-mCherry was injected into mouse zygotes (Liu, et al. (2012) *J. Neurosci.* 32:6600-6610). The offspring of ten founders were analyzed and five of them exhibited specific expression of mCherry in DCs/ PCs of *cochleae* at P33 and later stages after tamoxifen injection at P12/13 when bred with Fgfr3$^{icreER+}$. The obtained conditional transgenic mice showed no obvious abnormal cochlear morphology either with or without Isl1-induction in DCs/PCs. At least two independent lines (#4 and #18) phenocopied the synergistic effects of Isl1 and Atoh1 in this study. The analysis presented in this study is from #18.

RNA Sequencing.

*Cochleae* were dissected out, enzymatically digested, and triturated gently using firepolished Pasteur pipettes. The enzymatic digestion was performed by incubating the *cochleae* in 1 mg/ml pronase (Roche life science) at 37° C. for 40-50 minutes (Hempel, et al. (2007) *Nat. Protoc.* 2(11):2924-9). Total RNAs from handpicked fluorescently labeled isolated cells were purified as described previously (Hempel, et al. (2007) *Nat. Protoc.* 2(11):2924-9). The cDNAs were created and amplified using Single Primer Isothermal Amplification (SPIA) technology according to manufacturer's instructions (NuGEN, San Carlos, Calif.). Libraries for RNA sequencing were generated with Encore NGS Library Systems according to manufacturer's instructions (NuGEN). The 100-bp paired-end reads were generated using an ILLUMINA HISEQ 2000 system (Illumina, San Diego, Calif.). Base-calling was performed using Illumina Casava 1.7. FASTQ sequences adapter were trimmed (cutadapt) and mapped to the mouse mm9 genome by a pipeline that serially employs STAR and BWA as described previously (Ippagunta, et al. (2016) *Proc. Natl. Acad. Sci. USA* 113:E6162-E6171). The mouse mm9 genomic sequence file was obtained from Genecode. The mapping statistic was determined using FlagStat in SAMtools and the mapped reads were counted using HTSeq. The RNA-seq data is available at Gene Expression Omnibus (GEO) submission: GSE85983 (NCBI tracking system #18023366). The count matrix was trimmed mean of M-values (TMM)-normalized and the differential expressed genes were obtained using limma-voom package in R after adjusting p value into the false discovery rate (FDR) using Benjamini and Hochberg's adjustments (Benjamini & Hochberg (1995) *J. Roy. Stat. Soc. B Met.* 57:289-300). To obtain differentially expressed transcription factors, gene sets encoding transcription factors/regulators from the Animal Transcription Factor Database were used. Fragments per kilobase of exon per million fragments mapped (FPKM) value for each gene was calculated by dividing count of reads for each gene by total count of reads for each sample, multiply with 1,000,000, and dividing the number by each transcript length in kb. The transcript length for each transcript was calculated by adding up the length of all exons annotated for each gene from mm9 annotation file obtained from Genecode. All heatmaps were drawn using gplots package in R. To compare gene expression profiles from other laboratories, count matrix determined by RNA seq was combined with count matrix downloaded from GSE83357 (Maass, et al. (2016) *PLoS One* 11:e0167286). The combined count matrix was TMM-normalized and the differential expressed genes were determined using limma-voom package as described above. The differentially expressed genes with a false discovery rate (FDR)<0.001 included 1,168 genes. To determine optimal numbers of clusters, an average silhouette method was used in factoextra package. GO analysis was performed using DAVID Bioinformatics Resources 6.7. Only nonredundant GO terms were selected by using Revigo. Gene sets involved in stemness were obtained from. All boxplots were created using R.

Single-Cell Multiplex qPCR.

Total RNA (300 ng) extracted from the inner ear of a C57BL6 mouse at P1 was converted into cDNA using SUPERSCRIPT VILO Master Mix (Thermo Fisher Scientific). After adding 2× TAQMAN PreAmp Master Mix (Thermo Fisher Scientific) and 10× primer mix, preamplification of target genes was performed with 14 cycles of 95° C. for 15 seconds and 60° C. for 4 minutes. The cDNAs were treated with Exonuclease I (New England Biolabs, Beverley, Mass.), and the five-fold diluted cDNA was used to make a three-fold dilution series of 15 concentrations. The samples were mixed with 2× SSOFAST EVAGREEN Supermix with Low ROX (Bio-Rad, Richmond, Calif.) and 20×DNA Binding Dye Sample Loading Reagent (Fluidigm, South San Francisco, Calif.). They were combined with 2× Assay Loading Reagent and pooled primer pairs in the 48.48 Dynamic Array integrated fluidic circuit (IFC) (Fluidigm) using a BioMark IFC controller MX (Fluidigm). The quantitative PCR was performed using a BioMark HD system (Fluidigm). The limit of detection threshold cycle (LOD-Ct) value was determined from the highest Ct value obtained using a three-fold dilution series of 15 concentrations. The universal LOD-Ct was obtained by calculating the median value.

Handpicked fluorescent cells described above were lysed in 5 µL of lysis buffer containing 1× VILO reaction mix (Thermo), 1.2 U/L SUPERASE•IN RNase Inhibitor (Thermo Fisher Scientific), and 0.5% NP-40. The cDNA was generated in a 6-µL reaction volume after adding 0.15 µL of 10× SUPERSCRIPT Enzyme Mix (Thermo Fisher Scientific) and 0.12 µL of T4 Gene 32 Protein (New England Biolabs). The reverse transcription reactions were performed as recommended by Fluidigm. Pre-amplification of target genes was performed, and the five-fold diluted cDNA was used for subsequent quantitative PCR analysis as described above and Cq value of each gene for each cell were obtained using Fluidigm Real-Time PCR Analysis software. The Cq values were converted to expression levels using the equation $Log_2(Ex)=(LOD-Ct)$ value−Cq.

Cochleae were dissected out and incubated in solution (50% accutase (Innovative Cell Technologies, San Diego), 0.02% Trypsin (Thermofisher), 125 µg/ml, Thermolysin (SIGMA-ALDRICH)) at 37° C. for 3 minutes. Collagenase IV (0.02 mg/ml, SIGMA-ALDRICH) and dispase (Worthington Biochemicals Corp.) were added and the mixture was incubated for 4 minutes at 37° C. The enzymatically treated tissue was triturated gently using fire-polished pasteur pipettes and aggregated cells were removed using 40 µm strainer. The dissociated cells were centrifuged at 500×g for 5 minutes and resuspended in solution (0.5% fetal bovine serum, 0.04% bovine serum albumin, 0.3 mM ethylenediaminetetraacetic acid in Hanks' balanced salt solution). Library construction was performed using CHROMIUM™ Single Cell 3' v2 Reagent Kits (10× genomics) following the instruction manuals. Briefly, the dissociated cells were loaded into CHROMIUM™ Controller (10× Genomics) and the encapsulated cells were lysed individually. Reverse transcription within each oil droplet was performed and the cDNAs were amplified. Next generation sequencing was performed using an ILLUMINA HISEQ 4000 system (Illumina, San Diego, Calif.) and the sequence reads were aligned to mouse reference genome mm10 using Cell Ranger pipeline (10× Genomics). The obtained gene-barcode matrices were further analyzed using Seurat 1.4.0.16 in R. Briefly, cells with relatively small and large library size in individual datasets were individually removed as potential doublets and low-quality cells. Cell cycle classification was performed using scran 1.4.5 in R and cells classified as being in G1 phase were chosen. To minimize batch effects, expected counts were obtained by randomly generating numbers following binominal distribution with minimum number of total unique molecular identifier for all the cells as a parameter size and population of each gene as probability. Cell cycle-related, apoptosis-related, and ribosomal protein encoded genes were removed. Highly variable genes were chosen calculating the average expression and dispersion for each gene using MeanVarPlot function in the Seurat package with a default condition. Subsequent PCA followed by t-Distributed Stochastic Neighbor Embedding was performed. Differentially expressed genes were identified using FindAllMarkers function in the Seurat package with a default condition and PCA followed by tSNE analysis were further performed using the differentially expressed genes. Pseudo-temporal ordering analysis was performed using monocle 2.4.0 (Qiu, et al. (2017) *Nature Meth.* 14:979-82). Briefly, the expected counts were loaded into the monocle package with 0.5 lowerDetectionLimit and highly variable genes with 0.1 mean expression and ≥1.0 empirical dispersion for each gene were chosen. After these filtering genes, cell trajectory was drawn.

To create a machine learning classifier, 20% and 80% of cells from each cluster were chosen as test and training dataset using StratifiedShuffleSplit function from scikit-learn 0.9.0 in python 3.5.3. Gene expression for each gene was transformed into the range between 0 and 1 using MinMaxScaler function, PCA without whitening was performed using the training dataset, and 30 principle components were chosen. Optimal parameters for support vector machine with radial basal function such as C and gamma parameter were determined using GridSearch CV function with a default condition (3-fold cross validation). Predicted clusters for remaining 20% of cells were determined using predict function and the predicted clusters were compared to clusters determined by PCA followed by tSNE using confusion_matrix function.

Cochlear Explant Culture and Electroporation.

The organ of Corti from P0.5 FVB mice were dissected and electroporated as described previously (Masuda, et al. (2012) *Dev. Biol.* 372(1):68-80). Briefly, the organ of Corti was isolated with the basal hook region removed to allow for improved adhesion. The tissue was then transferred to 150 µL HBSS in the center of a Millipore filter membrane (30 mm-diameter culture plate insert; Millipore, Billerica, Mass.) with the sensory epithelium facing up. Excess HBSS was carefully removed, and 5 µL of plasmid (1 µg/µL) was immediately added on top of the tissue. The epithelium on the filter was then placed in the center of a dish electrode (anode, 2 mm-diameter flat round electrode; NEPA GENE). A cover electrode (cathode, 2 mm-diameter flat round electrode; NEPA GENE) was positioned above the epithelium. Two rectangular pulses were delivered (28 V, 30 ms duration, with a 970-ms interval) using the NEPA GENE CUY21EDIT Square Wave Electroporator. The organ of Corti was then left standing for 1 minute, after which 1 mL of OPTI-DMEM was added to the membrane. The explant was then divided in two on the filter membrane, and the apical and basal sections were transferred to separate 5-cm glass-bottom culture dishes (Mattek) coated with MATRIGEL reconstituted basement membrane preparation (Corning). A 2-mL volume of pre-warmed culture medium (high-glucose DMEM, 10% fetal bovine serum, 20 ng/mL epidermal growth factor, 10 uL/mL N2 supplement, 50 µg/mL ampicillin) was then added to each dish, and the dishes were incubated at 37° C. in 5% $CO_2$ and 95% humidity for the duration of the culture. All images in this study were taken at 7 days after transfection.

Database.

Gene sets encoding transcription factors/regulators were obtained from the Animal Transcription Factor Database. Gene sets involved in FGF signaling, Notch signaling, and WNT signaling were obtained from the Gene Ontology Consortium. Gene sets involved in JNK-STAT3 signaling were obtained from the Kyoto Encyclopedia of Genes and Genomes. Gene sets involved in sternness were obtained from the Broad Institute database. RNA expression profiles from other publications were found in the Gene Expression Omnibus (GEO) database (GSE60019, GSE56866).

Immunofluorescence and Quantification of Hair Cell Conversion Rate.

Primary antibodies used were as follows: Chicken anti-GFP antibody (1:1000, Abcam), Rabbit anti-Myosin VI (1:500 *Proteus* Bioscience), Mouse anti-Parvalbumin (1:500, Sigma), and Rabbit anti-mCherry (1:1000, Abcam). All images were taken under a Zeiss Axiophot 2 microscope with an LSM710 confocal laser scanning image system (Carl Zeiss, Jena, Germany).

To analyze the transfected explant cochleae, $GFP^+$ cells in the Greater Epithelial Ridge (GER) region of the Organ of Corti with no obvious abnormal shape were counted as transfected cells. Of the $GFP^+$ cells, Myosin $VI^+$ ($MyoVI^+$)/$GFP^+$ cells were counted as converted hair cells whereas $MyoVI^+/GFP^+$ cells within clusters containing cells with $MyoVI^+/GFP^+$ and with $MyoVI^+$ were considered dislodged endogenous cells. The ratio of $GFP^+/MyoVI^+$ cells to all $GFP^+$ cells was presented as the conversion rate while the transfection rate was defined by the number of $GFP^+$ GER cells par an explant.

To analyze cochleae from transgenic mice, 200-µm-long regions in the middle turn of the cochleae were chosen, as described previously (Liu, et al. (2012) *J. Neurosci.* 32:6600-10). $HA^+$ or $mCherry^+$ were ectopically expressed only in DCs and PCs in this study. The conversion rate was calculated as the percentage of $Parvalbumin^+/HA^+$ cells in all $HA^+$ cells (for all Atoh1-HA mice), $Parvalbumin^+/mCherry^+$ cells in all $mCherry^+$ cells (for all Isl1 mice), or $Parvalbumin^+/HA^+/mCherry^+$ cells in all $HA^+/mCherry^+$ cells (for all Atoh1-HA; Isl1 mice).

cDNA Construct.

Mouse Atoh1-HA and Isl1 cDNA were amplified using the Atoh1-HA transgenic plasmid (Liu, et al. (2012) *J. Neuorsci.* 32(19):6600-10) or inner-ear total RNA from C57BL6 mice at P1 and were subcloned into pCIG3.1. The following primers were used: for Atoh1, 5'-GCT CAT CGA TGA ATT CAT GTC CCG CCT GCT GCA T-3' (SEQ ID NO:2) and 5'-TAT CAC GCG TGA ATT CTT ATG CAT AGT CCG GGA CGT-3' (SEQ ID NO:3); and for Isl1, 5'-TTT GGC AAA GAA TTG CTC GAG CGC CAC CAT GGG AGA CAT GGG CGA TCC ACC AAA AAA AAA ACG-3' (SEQ ID NO:4) and 5'-GCA GAT ATC ACG CGT GAA TTC TCA TGC CTC AAT AGG ACT GGC TAC-3' (SEQ ID NO:5).

Single Cell RNA-Seq Profiles of SCs, HCs and cHCs in Juvenile and Adult Mouse Organs of Corti.

In contrast to other regenerative systems, the organ of Corti in the mature cochlea contains relatively few terminally differentiated cells: approximately 3,100 HCs, including both inner HCs (IHCs) and outer HCs (OHCS), similar numbers of Deiters' cells (DCs) and pillar cells (PCs) surrounding the OHCs, and several other SC subtypes surrounding the IHCs. Despite the paucity of HCs and SCs and the fragile structure of the mature cochlea, single cell RNA seq (10× Genomics) (Zheng, et al. (2017) *Nature Comm.* 8:14049) provided a promising avenue to dissect the molecular profiles of SCs, HCs and cHCs in mouse cochleae. These techniques allow the rapid and reliable determination of the 10% of transcripts most highly expressed in each cell (Zheng, et al. (2017) *Nature Comm.* 8:14049).

For HC conversion, the mouse model Fgfr3-iCreER; Atoh1-HA; a9-AChR-EGFP; tdTomato was used where ectopic expression of Atoh1-HA transgene was driven by Fgfr3-iCreER-mediated CAG promoter in DCs and PCs with tamoxifen induction at postnatal day 12-13 (P12) and, at P26 and P33, cHCs were double-positive for the reporters tdTomato and EGFP driven by the promotor of endogenous HC marker a9 AChR (Liu, et al. (2012) *J. Neurosci.* 32:6600-10; Zuo, et al. (1999) *Proc. Natl. Acad. Sci. USA* 96:14100-14105). After dissociating organs of Corti at P12, P26 and P33 during HC conversion, 5,470 single cell RNA-seq profiles were obtained from 8 organs of Corti from tamoxifen-induced or un-induced (control) mice. For profile analysis, individual cells were first placed into two-dimensional space based on their gene expression profiles using t-Distributed Stochastic Neighbor Embedding (tSNE) where cells with similar expression profiles form clusters. Overall, cells from P26 and P33 were evenly distributed within each cluster, as expected from mice with mature hearing (Narui, et al. (2009) *Internatl. J. Audiol.* 48:576-581). Occasionally, cells from P12 were placed at separate places from cells at other ages. It is possible that the cells from P12 were still developing and had distinct gene expression profiles from those at other ages. Overall, the distribution of cell types identified at P12, P26, and P33 was even across replicates, indicating that the dissociation protocol and single-cell RNA seq profiles were reproducible.

The tSNE analysis of single cell RNA seq profiles revealed a total of 21 clusters of cells from the organs of Corti at three time points. Based on expression of known genes for each cochlear cell type, these clusters were designated as HCs, DCs/PCs, Hensen cells, type I spiral ganglia, tympanic membrane border cells, Reisner membrane cells, immune and other cell clusters. For example, the cluster of DCs/PCs were defined as such because they expressed DC/PC-enriched markers. Similarly, the cluster of cHCs expressed many HC markers, GFP, Atoh1-HA transgene, and Fgfr3-iCreER-mediated tdTomato as expected. The clusters of IHCs and OHCs only contained specific HC markers and GFP but missed Atoh1-HA transgene or tdTomato.

Single-Cell RNA Seq Revealed a Continuum of Atoh1-Mediated Conversion.

Focusing on DC/PC (SC), IHC, OHC, and cHC clusters in detail, it was determined how DCs/PCs were progressively converted to cHCs at three time points. In this regard, 101 SCs, 60 HCs, and 145 cHCs were separated into seven clusters by tSNE, each expressing a collection of cell-type specific genes. To understand robustness of the unsupervised clustering analysis, 80% of cells from each cluster were randomly chosen as training datasets, Principle Component Analysis (PCA) was performed to convert large dimensional features (e.g., genes) into smaller number of dimensions (e.g., principle components), and a machine learning classifier was built using a support vector machine with a radial basis kernel function (rbf). The significant principle components and optimal parameters for the rbf kernel were determined using 3-fold cross-validation. The prediction accuracy of the remaining datasets (20%) using the classifier was 100%, thus validating the clusters identified by tSNE.

In support, Fgfr3 and Slc17a8 were expressed in clusters of SCs and IHCs, respectively, as well as other known markers in prospective clusters. SCs were further separated into two clusters: a majority of SC1 were from P12 cochleae while a majority of SC2 were from P26-33 cochleae, supporting the assertion that the SC1 cluster contained SCs that were the starting points for cHCs induced by ectopic Atoh1-HA. In the three clusters of cHCs, the endogenous Atoh1 was upregulated (more in the cHC2-3 clusters than in the cHC1). Similarly, Myo6 and Pou4f3 (two HC markers) were also expressed in cHCs (more in cHC3 than in cHC1-2). Thus, these analyses suggest that cHC1, cHC2 and cHC3 represented progressive stages of Atoh1-mediated conversion, while cHC3 was the final stage of Atoh1-mediated conversion that resembled postnatal immature HCs (Liu, et al. (2012) *J. Neurosci.* 32:6600-10; Walters, et al. (2017) *Cell Reports* 19:307-20).

To provide evidence for the trajectory of progressive conversion along with pseudo-time, pseudotemporal ordering analysis of SC1, cHC1-3 cells was performed using machine learning (Qiu, et al. (2017) *Nature Meth.* 14:979-982). The pseudo-time reconstruction placed individual cells in two-dimensional space based on transcriptional dynamics associated with HC conversion and they were uniformly located along the trajectory indicating a continuous conversion. It became clear that the conversion started from SC1 cluster (P12), progressed through cHC1-2 clusters and gradually reached the cHC3 cluster in a continuous manner. While transitioning from cHC1-2 to cHC3, more and more definitive HC markers (Myo6, Rasd2, Chrna9, Pvalb, Pou4f3, Chrna10) started to be expressed. Therefore, Atoh1-mediated conversion is a continuum from a donor SC to a target state that most closely resembled early postnatal differentiating HCs (Liu, et al. (2012) *J. Neurosci.* 32:6600-10; Walters, et al. (2017) *Cell Reports* 19:307-20).

To further delineate temporal progression of transcription factor expression during Atoh1-mediated conversion, the expression of transcription factors extracted by the machine learning was plotted along the conversion process from the initial donor SC1 state to the cHC3 state. Again SC-enriched transcription factors (i.e., Sox9, Id3, Hes5, and Rora/b) were gradually decreased while HC-markers (i.e., Atoh1, Barhl1, and Pou4f3) were concomitantly upregulated, further supporting the pseudo-time reconstruction.

Endogenous and Transgenic Atoh1 mRNA During the Conversion.

It was expected that during the conversion the endogenous Atoh1 would be upregulated by autoregulation (Helms, et al. (2000) *Development* 127:1185-96) and ectopic transgenic Atoh1-HA would be maintained at constant levels (because it is driven by the CAG promoter in SC1 cells upon Tam-induction). When endogenous and transgenic Atoh1 were analyzed separately for each cell from SC1 to cHC3 states, surprisingly it was observed that the expression of transgenic Atoh1-HA gradually increased from cHC1 toward cHC3 state and levels of both mRNAs were correlated among 145 cHC1-3 single cells as they were progressing toward the cHC3 state. These results suggested novel Atoh1 regulatory mechanisms.

Bulk RNA-Seg Profiling of Fluorescent-Labeled SCs, cHCs, and HCs in Mature Cochleae.

When using single-cell RNA seq, it is challenging to identify important transcription factors normally expressed at low levels. To identify differentially expressed transcription factors and to explore the entire transcriptome profiles, bulk single cell RNA seq was performed. Individual cells were manually isolated from genetically engineered mature mice, in which SCs (DCs and PCs) at P26, cHCs at P33, OHCs at P22, and IHCs at P74 had been specifically labeled with one or two fluorescent markers. Each combinatory genetic reporter mouse model allowed for the isolation of one cell type of interest with high purity under fluorescent microscope and 20 to 40 fluorescent cells were collected for each cell type (i.e., SC, cHC, IHC, and OHC) with biological two duplicates (Table 2). OHCs were also isolated at neonatal age P7 in a similar manner.

TABLE 2

| Cell Type | Mouse Lines | Tamoxifen | Age (bulk RNA-Seq) | Age (sc-qPCR) |
|---|---|---|---|---|
| SC | Fgfr3iCreER+; Rosa26-CAG-loxP-stop-loxP-tdTomato+ | P12 & 13 | P26 & 27 | P33 |
| cHC | Fgfr3iCreER+; Atoh1-HA+; α9 AChR-EGFP+; Rosa26-CAG-loxP-stop-loxP-tdTomato+ | P12 & 13 | P33 | P33 |
| OHC (P7) | PrestinCreERT2+; Rosa26-CAG-loxP-stop-loxP-tdTomato+ | P2 & 3 | P7 | N.A. |
| OHC | Prestin-YFP | N.A. | P22 & 23 | P33 |
| IHC | Pval-Cre+; Rosa26-CAG-loxP-stop-loxP-tdTomato+ | N.A. | P74 & 75 | N.a. |

A total of 10 bulk RNA-seq profiles (duplicates of five cell types) were obtained with normal ranges reported by others (Table 3)(Henry, et al. (2015) *Elife* 4:e09800). Among 34,590 annotated genes, expression of 23,415 genes were observed at least once in one of these cells. The RNA-seq profiles of biological duplicates for each cell type were highly reproducible (with a Spearman correlation of approximately 0.86-0.89) (Faherty, et al. (2015) *BMC Biotechnol.* 15:65). In support, a total of 14 genes that have been examined by immunostaining exhibited consistent expression patterns in HCs, cHCs or SCs (Liu, et al. (2012) *J. Neurosci.* 32:6600-10).

TABLE 3

| Cell Type | Cell # | Read # ($\times 10^6$) | Mapped % |
|---|---|---|---|
| SC (P26-27) | 36.5 ± 5.5 | 118 ± 53 | 83.0 ± 0.1 |
| cHC (P33) | 22.5 ± 0.5 | 121 ± 43 | 84.7 ± 1.6 |
| OHC (P7) | 29.5 ± 6.5 | 110 ± 44 | 84.1 ± 0.0 |
| OHC (P22-23) | 21 ± 0 | 67 ± 39 | 79.6 ± 7.1 |
| IHC (P74-75) | 85 ± 46 | 67 ± 1 | 79.6 ± 0.2 |

Independent Single-Cell Multiplex RNA-gPCR Analysis in Mature Cochleae.

To independently validate the bulk RNA-seq results at higher resolution, single-cell multiplex RT-qPCR analysis of 89 selected genes was carried out, as this approach has higher sensitivity than standard single-cell RNA seq methods. These genes included: (1) 52 genes encoding transcription factors (Table 1) that were identified as differentially expressed between cHCs (P33) and SCs (P26) or OHCs (P22) which normally had low levels of expression; (2) additional HC or SC marker genes (i.e., Slc26a5, Ocm, Gfi, Fgfr3, Cdkn1b, Gjb2); and (3) several housekeeping genes (i.e., Gapdh, Actb). Independent sets of single cells, including 27 SCs, 25 cHCs, and 16 OHCs, were isolated after enzymatic cochlear dissociation at P33 in the same genetic mouse models (Table 2) and analyzed with a Fluidigm BIOMARK HD system after primer validation.

Single-cell multiplex qPCR results of 89 genes in SCs (P33), cHCs (P33) and OHCs (P33) provided correlation coefficients between bulk RNA-seq and single-cell qPCR methods of 0.83-0.90, further demonstrating the reliability of the bulk RNA-seq and single-cell qPCR results.

Differentially Expressed Transcription Factors that Promote Atoh1-Mediated SC-to-HC Conversion In Vivo.

To identify differentially expressed genes between cHCs and SCs or HCs that needed to be further manipulated to promote the efficiency and completion of Atoh1-mediated HO conversion in vivo, bulk RNA-seq profiles were further analyzed.

First, gene expression profiles between SCs (P26) and OHCs (P22) were compared and 1,607 differentially expressed genes were found with statistical significance. Among those genes, 781 genes were significantly enriched in SCs (P26) and 826 in OHCs (P22). When gene expression profiles were compared between SCs (P26) and cHCs (P33), 783 differentially expressed genes were found. Among those genes, 280 genes were significantly enriched in SCs (P26) and 503 in cHCs (P33). As expected, Atoh1 was highly enriched in cHCs (P33), consistent with the single-cell RNA seq results. Similarly, direct comparison between cHCs (P33) and OHCs (P22) showed that 476 genes were enriched in cHCs (P33) and 396 genes remained lacking in cHCs (P33) including Slc26a5 and Ocm compared to OHCs (P22). GO enrichment analysis was also performed using gene sets classified above identifying enriched HC function genes (FDR<0.05).

To identify transcription factors that promote Atoh1-mediated conversion of SCs to HCs in vivo, focus was placed on transcription factors that were differentially expressed among mature SCs (P26), cHCs (P33), and mature OHCs (P22) from the bulk RNA-seq results. Among 1,425 transcription factors in the mouse genome, 90 transcription factor genes were identified that were differentially expressed, with statistical significance, in SCs (P26), cHCs (P33), and OHCs (P22). These 52 genes (Table 1) were independently validated by single-cell qPCR analysis.

Isl1 Synergistically Enhances the Rate of Atoh1-Mediated SC-to-HC Conversion Ex Vivo and In Vivo.

To further validate the functional activities of these transcription factor genes in Atoh1-mediated SC-to-HC conversion, one of the genes, Isl1, was tested because Isl1 deletion has been shown to down-regulate Mlxip, Zbtb38, Aff3, Zfp827, and Zfp532 in cardiac pacemaker cells (Liang, et al. (2015) *J. Clin. Invest.* 1225:3256-68) as well as Tub in retinal cells (Mu, et al. (2008) *Proc. Natl. Acad. Sci. USA* 105:6942-7), all of which are transcription factors identified herein with similar differential expression patterns as Isl1.

For this analysis, Isl1 was overexpressed in cochlear explants, which were used as surrogates in studies of in vivo cochlear SC-to-HC conversion because progenitor-like cells in the medial region (the greater epithelial ridge [GER]) of the cochlear explant were converted to HCs by Atoh1 transfection (Zheng & Gao (2000) *Hear Res.* 349:182-96). When cochlear explants were transfected with plasmids containing vector (GFP) alone, Atoh1, Isl1, or both Atoh1 and Isl1, a significant increase in the number of transfected GER cells converted into Myo6-expressing HC-like cells was observed when both Atoh1 and Isl1 were transfected, whereas Isl1 itself did not convert the GER cells. The increase in the conversion rate in Atoh1-Isl1 co-transfected cochleae was nearly double that in cochleae transfected with Atoh1 alone (43.9% vs. 25.5%), while the transfection rates among the four groups were similar (approximately 200-250 GFP$^+$ cells/explant). No significant difference in Ki67 staining was observed among transfected GER cells (GFP$^+$) between explants transfected with Atoh1 alone and Atoh1+Isl1 (1.3% vs. 1.1%), indicating no significant proliferation induced by the co-transfection.

To validate Isl1 function in vivo, transgenic mouse lines were created to ectopically express Isl1 and to test whether the Isl1 expression in SCs synergistically enhances Atoh1-mediated conversion in vivo. Indeed, co-expressing Isl1 in SCs significantly increased the conversion rate compared with Atoh1 alone (50% vs 13%) at P33, three weeks after Tam-induction (at P12). Expression of Isl1 alone, in contrast, failed to promote any conversion from SCs to HCs. Together, the ex vivo and in vivo results clearly demonstrate that Isl1 synergistically enhances Atoh1-mediated SC-to-HC conversion by increasing the conversion rate. Moreover, the results validate the bulk and single cell RNA-seq and single-cell qPCR analyses, indicating that the other transcription factors identified herein can also promote Atoh1-mediated conversion.

Example 2: Role for NuRD and PRC2 in the Mammalian Inner Ear

Cellular reprogramming offers tremendous potential for therapeutics, disease studies, and developmental processes. However, direct reprogramming through ectopic expression of defined transcription factors is often a slow and inefficient process with most cells failing to reprogram. In the auditory field, ectopic expression of Atoh1 has been used to convert mammalian SCs into cells that express many endogenous HC markers. In vivo studies of HC regeneration found that induction of ectopic Atoh1 in SCs during the first postnatal week, leads to the formation of HC-like cells. However, induction of Atoh1 at later postnatal ages (P8-P14) showed a dramatic decrease in SC conversion, and by P30, induction of Atoh1 alone no longer leads to the formation of HC-like cells. These data suggest that cochlear SCs lose their cellular plasticity and capacity for cellular reprogramming during inner ear development.

The loss of reprogramming potential in the inner ear has remained a central unresolved question in the auditory field. Cellular reprogramming studies in other systems have shown that the epigenetic memory of the donor cell can greatly impact its ability to be reprogrammed. To address whether similar epigenetic mechanisms also limit the ability of SCs to become HCs, the role of repressive histone modifying complexes such as the nucleosome remodeling and deacetylation (NuRD) complex and polycomb repressive complex 2 (PRC2) were analyzed. NuRD and PRC2 are highly conserved and required for gene silencing during multiple developmental processes. Using the cre-lox system at late embryonic and neonatal time points, it was found that conditional loss of PRC2 or the NuRD enzymatic subunit Lsd1 causes no obvious phenotypic defect in organ of Corti development. However, loss of these factors does cause alterations in the expression of key developmental signaling pathways such as the Notch pathway.

Since Notch regulation has been implicated as a factor limiting inner ear reprogramming, mice were generated that have Cre-mediated ectopic Atoh1 expression combined with loss of PRC2 or Lsd1. Interestingly, loss of either of these factors combined with ectopic Atoh1 expression results in a dramatic increase in reprogramming potential that includes a large increase in reprogramming efficiency and, for the first time, terminal differentiation of some reprogrammed cells. In particular, reprogrammed cells express mature inner hair cell markers, otoferlin and vGlut3. However, loss of Lsd1 or PRC2 at later ages does not increase reprogramming potential. Altogether these data indicate that PRC2 and NuRD negatively regulate genes that are vital for maintaining cellular plasticity but are not required for terminal differentiation of cells in the organ of Corti. Therefore, combining Atoh1 gene therapy with inhibitors of PRC2 or NuRD (e.g., RNAi or small molecule inhibitors that block Lsd1 or Eed expression, or CRISPR/Cas9 and viral vector-based approaches) can facilitate the regeneration of functional HCs and hearing restoration.

What is claimed is:

1. A method of increasing hair cell conversion rate comprising administering to the inner ear of an animal in need thereof a first nucleic acid molecule encoding Atoh1 and a second nucleic acid molecule encoding Isl1 wherein the first and second nucleic acid molecules are co-expressed from the same or different expression constructs.

* * * * *

SEQUENCE LISTING

```
<160> NUMBER OF SEQ ID NOS: 5

<210> SEQ ID NO 1
<211> LENGTH: 21
<212> TYPE: PRT
<213> ORGANISM: Artificial sequence
<220> FEATURE:
<223> OTHER INFORMATION: Synthetic peptide

<400> SEQUENCE: 1

Ala Ala Asn Ala Arg Glu Arg Arg Arg Met His Gly Leu Asn His Ala
```

```
1               5                   10                  15
Phe Asp Gln Leu Arg
            20
```

<210> SEQ ID NO 2
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 2
gctcatcgat gaattcatgt cccgcctgct gcat                           34

<210> SEQ ID NO 3
<211> LENGTH: 36
<212> TYPE: DNA
<213> ORGANISM: Artificial sequence
<220> FEATURE:
<223> OTHER INFORMATION: Synthetic oligonucleotide

<400> SEQUENCE: 3
tatcacgcgt gaattcttat gcatagtccg ggacgt                         36

<210> SEQ ID NO 4
<211> LENGTH: 63
<212> TYPE: DNA
<213> ORGANISM: Artificial sequence
<220> FEATURE:
<223> OTHER INFORMATION: Synthetic oligonucleotide

<400> SEQUENCE: 4
tttggcaaag aattgctcga gcgccaccat gggagacatg ggcgatccac caaaaaaaaa   60
acg                                                             63

<210> SEQ ID NO 5
<211> LENGTH: 45
<212> TYPE: DNA
<213> ORGANISM: Artificial sequence
<220> FEATURE:
<223> OTHER INFORMATION: Synthetic oligonucleotide

<400> SEQUENCE: 5
gcagatatca cgcgtgaatt ctcatgcctc aataggactg gctac                45